US008877818B2

(12) United States Patent
Neas et al.

(10) Patent No.: US 8,877,818 B2
(45) Date of Patent: Nov. 4, 2014

(54) ANTIMICROBIALLY ACTIVE COMPOSITIONS

(75) Inventors: Edwin Dean Neas, Nunn, CO (US); Jerald Edward Kuiken, Windsor, CO (US); John Louis Schenk, Fort Collins, CO (US); Thomas Boyd Gilligan, Fort Collins, CO (US)

(73) Assignees: XY, LLC, Navasota, TX (US); CHD Bioscience, Inc, Fort Collins, CO (US)

( * ) Notice: Subject to any disclaimer, the term of this patent is extended or adjusted under 35 U.S.C. 154(b) by 1312 days.

(21) Appl. No.: 11/804,879

(22) Filed: May 21, 2007

(65) Prior Publication Data

US 2008/0090917 A1  Apr. 17, 2008

Related U.S. Application Data

(63) Continuation of application No. 11/400,839, filed on Apr. 6, 2006.

(60) Provisional application No. 60/669,912, filed on Apr. 7, 2005.

(51) Int. Cl.
*A61L 2/18* (2006.01)
*A01N 35/02* (2006.01)
*A01N 35/06* (2006.01)
*A01N 25/00* (2006.01)
*A01N 31/02* (2006.01)

(52) U.S. Cl.
CPC . *A61L 2/18* (2013.01); *A01N 25/00* (2013.01); *A01N 35/02* (2013.01); *A01N 35/06* (2013.01); *A01N 31/02* (2013.01)
USPC .......................................... 514/675; 514/724

(58) Field of Classification Search
None
See application file for complete search history.

(56) References Cited

U.S. PATENT DOCUMENTS

| | | | |
|---|---|---|---|
| 1,654,103 A | 12/1927 | Thomson | |
| 2,192,119 A * | 2/1940 | Woodhouse | 252/366 |
| 3,756,459 A | 9/1973 | Bannister et al. | |
| 4,796,788 A | 1/1989 | Bond | |
| 4,870,108 A * | 9/1989 | Page | 514/642 |
| 5,492,534 A | 2/1996 | Athayde et al. | |
| 5,559,032 A | 9/1996 | Pomeroy et al. | |
| 5,665,315 A | 9/1997 | Robert et al. | |
| 5,672,764 A | 9/1997 | Teissier et al. | |
| 5,690,815 A | 11/1997 | Krasnoff et al. | |
| 5,799,830 A | 9/1998 | Carroll et al. | |
| 5,888,823 A | 3/1999 | Matsumoto et al. | |
| 5,893,843 A | 4/1999 | Rodrigues Claro | |
| 5,919,360 A | 7/1999 | Contaxis, III et al. | |
| 5,934,885 A | 8/1999 | Farrell et al. | |
| 6,086,574 A | 7/2000 | Carroll et al. | |
| 6,228,354 B1 * | 5/2001 | Jeng | 424/78.07 |
| 6,251,615 B1 | 6/2001 | Oberhardt | |
| 6,328,071 B1 | 12/2001 | Austin | |
| 6,495,366 B1 | 12/2002 | Briggs | |
| 6,593,283 B2 | 7/2003 | Hei et al. | |
| 6,698,627 B2 | 3/2004 | Garcia et al. | |
| 6,729,369 B2 | 5/2004 | Neas et al. | |
| 6,752,298 B2 | 6/2004 | Garcia et al. | |
| 6,761,286 B2 | 7/2004 | Py et al. | |
| 6,761,288 B2 | 7/2004 | Garcia | |
| 6,789,706 B2 | 9/2004 | Abergel et al. | |
| 6,789,750 B1 | 9/2004 | Heldt | |
| 6,793,387 B1 | 9/2004 | Neas et al. | |
| 2001/0023253 A1 | 9/2001 | Craig et al. | |
| 2001/0051379 A1 | 12/2001 | Pucher | |
| 2003/0095897 A1 | 5/2003 | Grate et al. | |
| 2003/0113673 A1 | 6/2003 | Ahn et al. | |
| 2004/0107150 A1 | 6/2004 | Neas et al. | |
| 2004/0246321 A1 | 12/2004 | Takashima et al. | |
| 2005/0003020 A1 | 1/2005 | Smith | |
| 2005/0011582 A1 | 1/2005 | Haug | |
| 2005/0031994 A1 | 2/2005 | Banba et al. | |
| 2005/0080194 A1 | 4/2005 | Satake et al. | |
| 2005/0209223 A1 | 9/2005 | Das et al. | |
| 2006/0118167 A1 | 6/2006 | Neas et al. | |
| 2006/0257436 A1 | 11/2006 | Kaminuma et al. | |
| 2006/0263399 A1 | 11/2006 | Yasuna et al. | |
| 2006/0293214 A1 | 12/2006 | Cheng et al. | |
| 2007/0053866 A1 | 3/2007 | Abou-Nemeh | |
| 2009/0076169 A1 | 3/2009 | Neas et al. | |

FOREIGN PATENT DOCUMENTS

| | | | |
|---|---|---|---|
| BE | 1003325 | * | 2/1992 |
| JP | 06240296 | | 8/1994 |
| WO | WO 2006/060770 | | 6/2006 |
| WO | WO 2006/110553 | | 10/2006 |
| WO | WO 2009/038672 | | 3/2009 |

OTHER PUBLICATIONS

English Abstract of BE-1003325, Derwent Acc. No. 1992-105054 (1992).*
Office Action mailed on May 6, 2008 for U.S. Appl. No. 11/400,839; 13 pages.
Office Action mailed on Aug. 19, 2008 for U.S. Appl. No. 11/400,839; 12 pages.
Office Action mailed on May 13, 2009 for U.S. Appl. No. 11/400,839; 24 pages.
Office Action mailed on Feb. 3, 2010 for U.S. Appl. No. 11/400,839; 20 pages.
Conner et al., Vapor-Liquid Equilibria in Binary Systems, Industrial and Engineering Chemistry, vol. 42, No. 1, 1949, pp. 106-110.
Document Summary, Active Standard:ASTM D7094-04 Standard Test Method for Flash Point by Modified Continuously Closed Cup (MCCCFP) Tester, http://www.astm.org, Aug. 16, 2007, 2 pp.
Hack et al., Vapor-Liquid Equilibria of the Diacetone Alcohol-Water System at Subatmospheric Pressures, Industrial & Engineering Chemistry, vol. 46, No. 11, 1954, pp. 2392-2395.
Germicidal Spray Products as Disinfectants, http://www.eoma.aoac.org/methods, Aug. 16, 2007, one page.

(Continued)

*Primary Examiner* — David J Blanchard
*Assistant Examiner* — Barbara Frazier
(74) *Attorney, Agent, or Firm* — Craig R. Miles; CR Miles, P.C.

(57) ABSTRACT

Compositions (3) and methods of using such compositions (3) to condition, clean, or disinfect the flow path of a conduit (8) of a microfluidic devices (16), such as flow cytometers or liquid chromatographs.

8 Claims, 14 Drawing Sheets

(56) References Cited

OTHER PUBLICATIONS

Product Properties Test Guidelines, OPPTS 830.7200 Melting Point/Melting Range, EPA, Prevention, Pesticides & Toxic Substances(7101), EPA712-C-96-033, Aug. 1996, 5 total pages.

Product Properties Test Guidelines, OPPTS 830.7200 Boiling Point/Boiling Range, EPA, Prevention, Pesticides & Toxic Substances(TS7101), EPA712-C-96-034, Aug. 1996, 13total pages.

Slow-Stirring Method for Determining the n-Octanol/Water Partition Coefficient . . . , Environmental Toxicology & Chemistry, http://www.setacjournals.org, Aug. 16, 2007, pp. 1051-1057.

Sorting of Bacteria, Current Protocols in Cytometry, 1999, Supplement 7, Unit 11.4, pp. 11.4.1-11.4.12.

U.S. Appl. No. 60/669,912, filed Apr. 7, 2005 entitled "Flow Path Conditioner System".

U.S. Appl. No. 11/400,839, filed Apr. 6, 2006 entitled "Flow Path Conditioner System".

Office Action mailed Oct. 6, 2010 for U.S. Appl. No. 11/887,872.

Cooper. The influence of organic solvents on the bactericidal action of the phenols. Chemical Abstracts Service, Dec. 2001, abstract, 1 page.

Cooper. The influence of organic solvents on the bactericidal action of the phenols. J of the Society of Chemical Industry, 1945, vol. 64, pp. 51-53, London.

Davies. Flow Cytometry: Principles and Application, Chapter 11: Cell Sorting by Flow Cytometry; in: Flow Cytometry: Principles and Applicatios, Humana Press, Totowa, NJ, 2007, pp. 257-276.

Furuta et al. Antimicrobial activity of water-soluble solvents: relation to hydrophobic parameters and chemical structure. Chemical Abstracts Service, Dec. 1993, abstract, 1 page.

Furuta et al. Antimicrobial activity of water-soluble solvents: relation to hydrophobic parameters and chemical structure. J Antibact. Antifung. Agents, 1993, vol. 21, No. 8, pp. 439-444, Japan.

Hack et al. Vapor-liquid equilibria of the diacetone alcohol-water system at subatmospheric pressures. Industrial & Engineering Chemistry, vol. 46, No. 11, Nov. 1, 1954, pp. 2392-2395.

Hsueh. Maintenance of the AutoMACS Cell Sorter. Retrieved from the Internet: http://www.signaling-gateway.org, originally downloaded Mar. 16, 2012, 2 total pages.

Schmid et al. Boisafety Guidelines for Sorting of Unfixed Cells. Cytometry, Jan. 1997, vol. 28, pp. 99-117.

Office Action mailed Aug. 17, 2011 for U.S. Appl. No. 11/887,872.

Patsch et al. Der Einfluss verschiedener organischer Losungsmittel auf das Wachstum von Bakterien. Zeitschrift fur Allg. Mikrobiologie, 1971, vol. 11, iss.1, pp. 49-56.

Patsch et al. English translation of abstract: Influence of various organic solvents on the growth of bacteria. Zeitschrift fur Allg. Mikrobiologie, 1971, vol. 11, iss.1, pp. 49-56.

Corresponding European patent application 06740742.9; OA mailed Apr. 18, 2012, 12 total pages.

BD Biosciences. BD Accuri™ C6 Flow Cyrometer Instrument Manual. 7820018 Rev-2, 2012, 30 total pages.

BD Biosciences. BD FACSCanto II Flow Cytometer Reference Manual, May, 2006, 158 total pages.

Harkins. Sorting of Bacteria; Current Protocols in Cytometry, Jan. 1999, pp. 11.4.1-11.4.12.

McIntyre, et al. Decontamination of the BD FACSAria II or BD FACSAria III System Using the Prepare for Aseptic Sort Procedure. Application Note; BD Biosciences, Jul. 2010, 7 total pages.

Schmid, et al. Biosafety Concerns for Flow Cytometric HIV Innunophenotyping: Questions and Answers; http://cyto.mednet.ucla.edu/Protocols/BiosafetysectionforNIHmanualQA.pdf; downloaded Apr. 29, 2013, 14 total pages.

Stanford Stem Cell Institute Flow Cytometry Core. Preparation for Aseptic Sorting in the Flow Cytometry Lab; Jun. 2011, 3 total pages.

Office Action mailed on Mar. 22, 2010 for U.S. Appl. No. 11/887,872.

Office Action mailed on Aug. 17, 2011 for U.S. Appl. No. 11/887,872.

Office Action mailed on Jan. 13, 2012 for U.S. Appl. No. 11/887,872.

Office Action mailed on Sep. 4, 2012 for U.S. Appl. No. 11/887,872.

Chem-Star Dairy Sanitation. Exspor® Activator Exspor® Base. Website, chemstarworks.com/wp-content/uploads/2009/07/ExsporBase-ActivatorCatalogSheet1.pdf, originally downloaded May 23, 2014, 2 total pages.

* cited by examiner

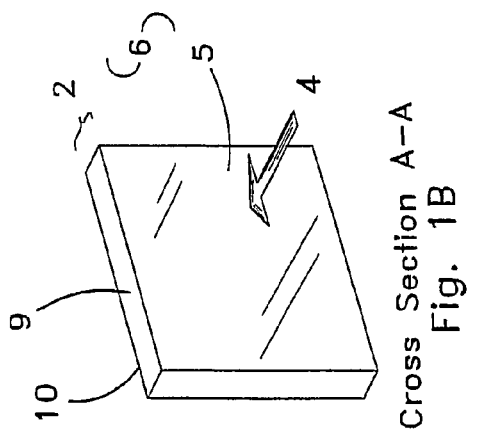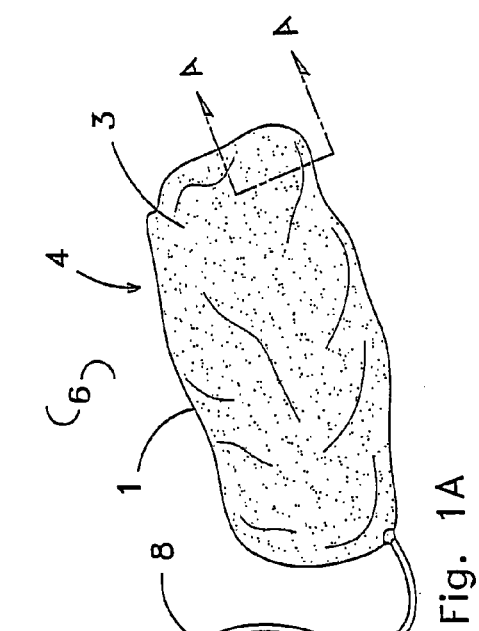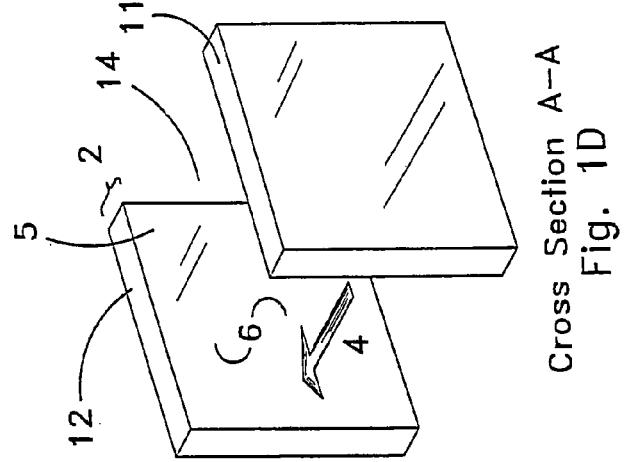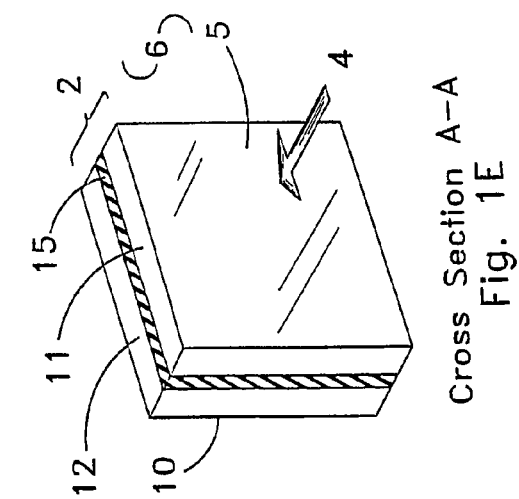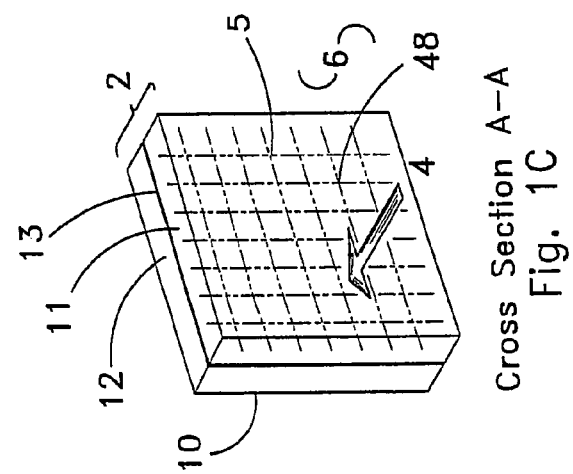

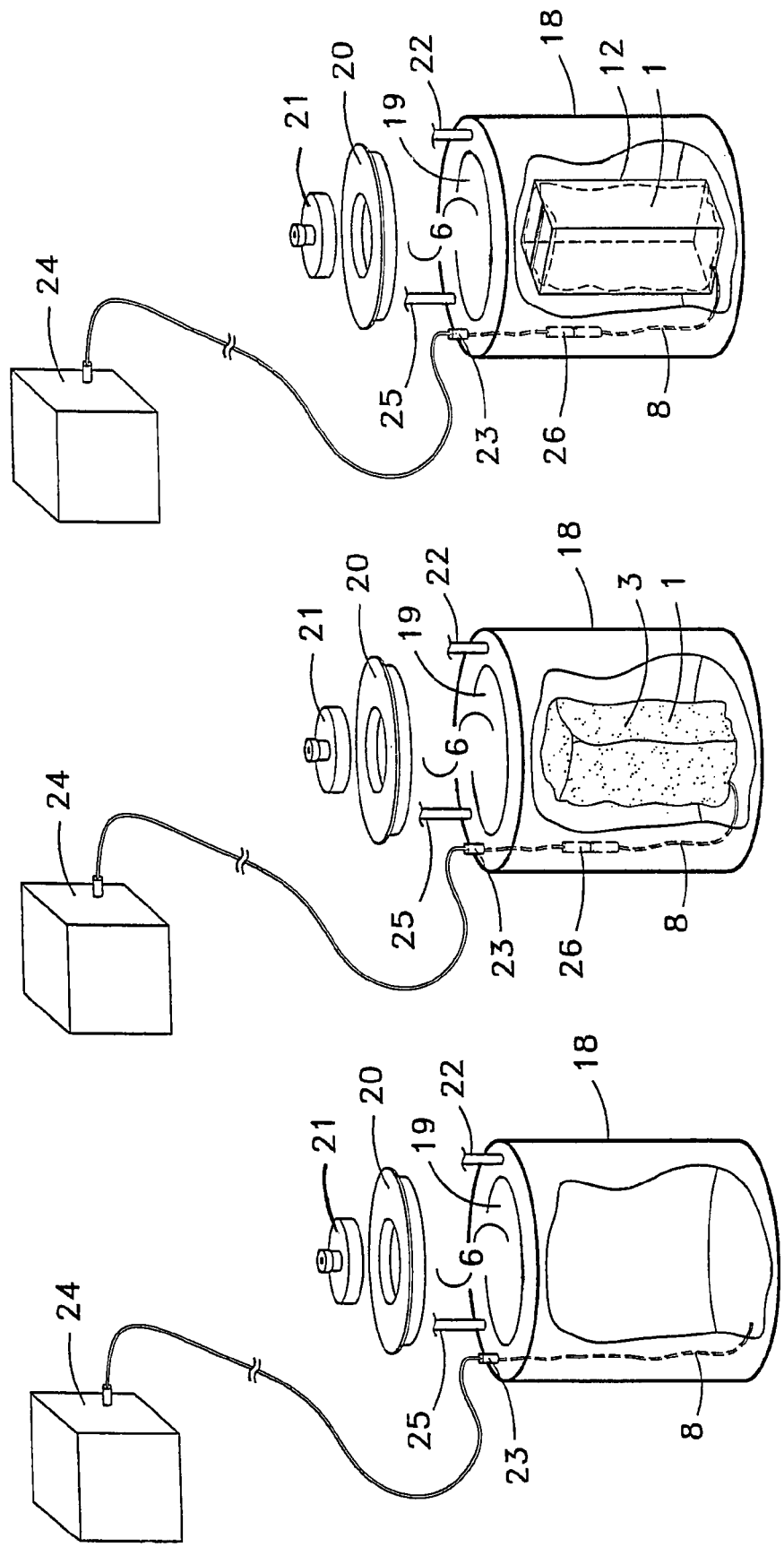

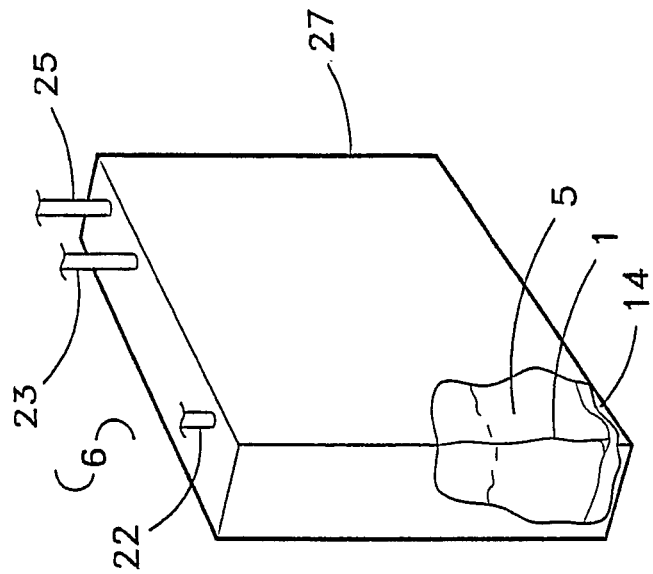
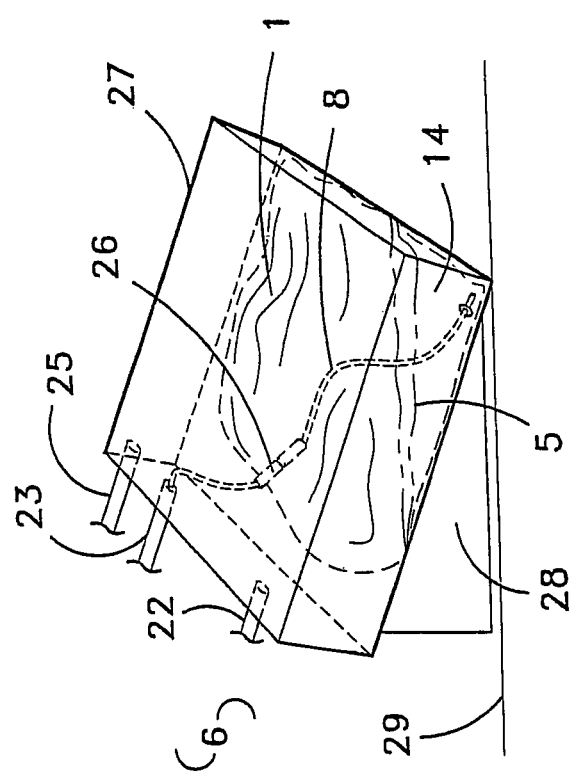
Fig. 3B
Fig. 3A

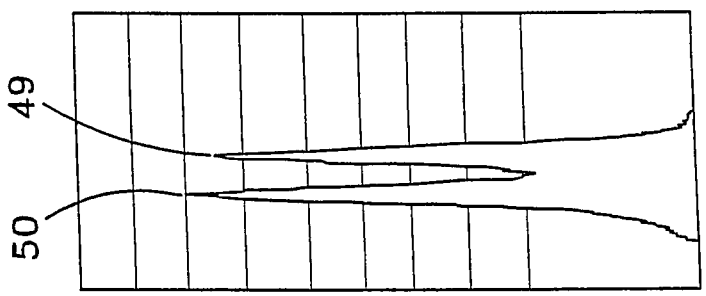
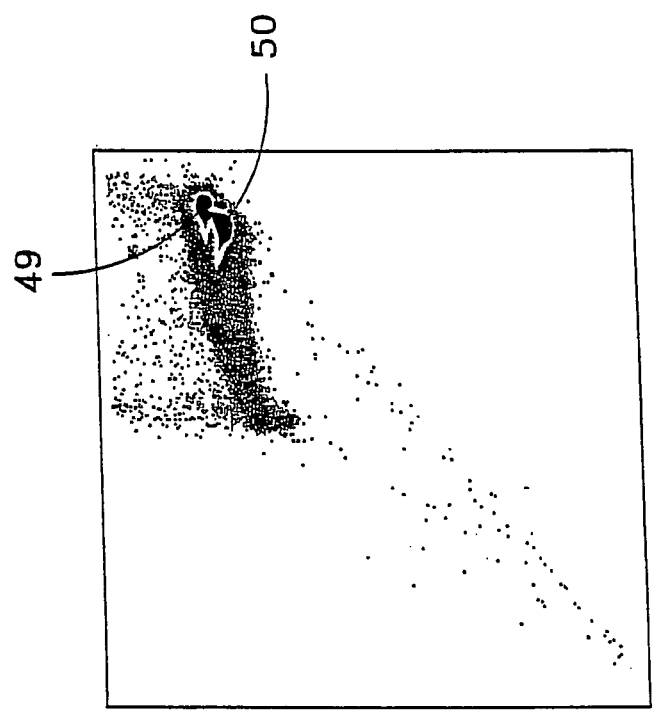
Fig. 6

ANTIMICROBIALLY ACTIVE COMPOSITIONS

This United States Patent application is a continuation of U.S. patent application Ser. No. 11/400,839, filed Apr. 6, 2006, and claims the benefit of U.S. Provisional Patent Application No. 60/669,912, filed Apr. 7, 2005, each hereby incorporated by reference herein.

I. TECHNICAL FIELD

Compositions and methods of using such compositions to condition, clean, or disinfect the flow path of microfluidic devices, such as flow cytometers or liquid chromatographs.

II. BACKGROUND

Flow cytometry, liquid chromatography, and other microfluidic devices are prominent tools used in basic and applied research and in commercial manufacturing processes. These microfluidic systems are routinely used to analyze, separate, isolate, or purify biological particles, such as cells, organelles, chromosomes, deoxyribonucleic acids (DNA), ribonucleic acids (RNA), DNA fragments, RNA fragments, proteins, protein fragments, peptides, oligonucleotides, or the like.

Specifically with respect to applications in flow cytometry or the utilization of flow sort devices, biological particles, such as cells (which may be modified with one or a plurality of ligands, labels, or fluorescent dyes), or carrier particles (which can bear biological particles such as antibodies or oligonucleotides, or the like), can be analyzed and sorted to isolate individual cells or biological particles, or subpopulations of cells or biological particles, having one or a plurality of common characteristic(s). As the field of flow cytometry and other microfluidic devices has matured, an increased emphasis has been placed on retaining the biological function(s) of isolated cells or biological particles.

Flow cytometers can also be used to analyze and sort a mixture of non-biological particles. For example, non-biological particles may be differentially modified with analyte specific reagents and reacted with a heterogeneous mixture of biological particles or analytes. The non-biological particles loaded with the corresponding reagent specific biological particles or analytes can then be differentiated and isolated with the flow sort system. Flow sort applications of this type can provide epitope or gene sequence analysis similar to that of a microarray analysis which utilizes a flat surface, such as a microscope slide, to present different analyte specific reagents such as antibodies, oligonucleotides, aptamers, or the like, to one or more biological particles of a heterogeneous biological mixture.

To maintain the biological function(s) of living cells during analysis, separation, purification, or collection, cells are entrained in fluids prepared to have certain characteristics relating to, purity, pH, ion concentration, osmolality, buffering capacity, nutrient availability, and the like. With respect to certain applications, these fluids must be prepared with water validated to be free of adventitious agents, pyrogens, or the like; or with chemicals obtained from chemical suppliers validated as in compliance with regulatory specifications such as cGMP guidelines, 510K guidelines, ISO-9000 type guidelines, batch record documentation, drug master file documentation, or the like.

Specifically with respect to chromatographic systems, the fluids used to entrain and separate biological particles are often purified mixtures of solvents and solutes in water. Variable mixture between two or more fluids to establish differential gradients of salt concentration, pH, solvent ratios, or the like may be utilized to selectively release particles from a variety of solid substrates to effect the separation of biological particles into subpopulations based upon one or more particle characteristics.

Characteristic of chromatographic systems is the relatively large volume of fluid used to separate mixtures of different particle(s) or population(s) of particles into individual particles or purified subpopulations of particles which are then isolated in a relatively small volume of fluid. Typically, many liters of an elution buffer may be collected in a plurality of individual fractions each containing just a few milliliters with the desired product isolated in one or few of such fractions. The preparation and handling of fluids to support chromatographic applications must be performed reliably by appropriately trained technicians. Any inaccuracy in the preparation of such fluids can lead to significant loss of chromatograph operating time or loss in whole or in part of the unpurified mixed particle(s) or population(s) of particles or of the purified individual particle(s) or subpopulation(s) of particles of interest.

Understandably, extensive research has been conducted resulting in numerous and varied types of microfluidic devices, compositions or fluids utilized with such microfluidic devices, and methods of making and using such microfluidic devices to separate biological and non-biological particles as above-described, or otherwise. Nonetheless, significant problems remain unresolved with regard to establishing and maintaining consistency in the preparation, handling, and delivery of fluids to and in the flow paths of such microfluidic devices; reducing or eliminating flora and fauna in the flow paths of such microfluidic devices; and cleaning, conditioning and disinfecting the surfaces of the conduits which define the flow paths of such microfluidic devices.

A significant problem with conventional delivery of fluids to microfluidic devices can be contamination of the fluid. The transfer of fluid from a fluid reservoir to a microfluidic device, and further transfer of the fluid through the various analytical conduits may require generation of hydrostatic pressure. Typically, a pump supplies the hydrostatic pressure required to move a fluid to and in the conduits of a microfluidic device.

Positive displacement pumps, for example, take up fluid from one side of the pump body, and utilizing valves, pistons, rotors, paddles, or the like, force the fluid to the other side of the pump. In this process, the fluid may come into contact with the internal surfaces of the pump depositing non-biological or biological materials, microbial or other infectious agents, which may remain within the body of the pump. In this way, the surfaces of the pump body can become a source of contamination to the subsequent volume of fluid transferred through the pump body.

Peristaltic pumps, apply pressure to the exterior surface of a conformable conduit to act on fluids contained within the conformable conduit. Peristalsis of the conformable conduit transfers fluid in one direction within the body of the conformable conduit. An advantage of the peristaltic pump can be that fluids do not contact the surfaces of the peristaltic pump. However, peristaltic pumps have disadvantages in that they may not build very high pressures, may tend to create oscillating hydrostatic pressure variations, may be expensive to build and maintain, and recurring peristalsis of the conformable conduit can cause progressive deformation or degradation of the conduit material which can shed, bleed, or leach into the fluid.

Another significant problem with conventional delivery of fluids to microfluidic devices can be the use of a gas or mixtures of gases, such as air, argon, nitrogen, helium, or the like, to pressurize the head space of a fluid reservoir to initiate and maintain a fluid stream in the conduits of the microfluidic device. Use of pressurized gas(es) or atmospheric gas pressure in contact with fluid in the reservoir can result in bubble formation in the fluid paths of the device. Since microfluidic devices have small diameter flow paths and the biological particles entrained in the fluid stream are also of small size, even very small or fine bubbles formed in the flow path can affect volume and laminar flow of the fluid within the flow paths, can cause failure of certain types of pumps, and can result in analytical errors. Even bubbles invisible to the naked eye can be problematic with respect to the proper performance of a microfluidic device.

One mechanism by which unwanted bubbles may spontaneously form in the flow path of a microfluidic device can be a change in the concentration of dissolved gas in the liquid stream followed by bubble formation. For example, a sheath fluid reservoir may contain an amount of sheath fluid to operate a flow cytometer for a long duration of time, sometimes in excess of 72 hours. With a head pressure of more than four atmospheres, or in certain applications in excess of 6 atmospheres, dissolved nitrogen content of the fluid can dramatically increase as the gases in the liquid move toward equilibrium with the gases in the head space of the reservoir.

Subsequently, when gas pressure on the liquid is reduced, bubbles may form. Reduction in gas pressure may come from operator inspection or manipulation of the amount of fluid remaining in the sheath fluid reservoir. Alternately, as the fluid flows through the conduits of the microfluidic device, fluid pressure may become substantially lower to match the operating pressure of the microfluidic flow path. Under these conditions bubbles may form and travel within the flow path of the microfluidic device. Alternately, surface tension of the bubble may allow it to adhere to the surfaces of the analytical components of the microfluidic device. Adhered bubbles may further serve as nuclei of condensation where additional small bubbles fuse, or where additional dissolved gas may enter the bubble.

The position of such bubbles partitioning between a surface adherent phase, and the fluid suspended phase, is determined by the size of the bubble, and the rate of flux of the fluid at that point in the apparatus. Microfluidic devices, flow cells, and flow cytometers commonly present regions in the flow path where flow is not laminar, where flux rate is low, and where bubbles tend to form. For example, microfluidic devices may have filters which purposefully restrict the fluid flow to facilitate removal of unwanted particles or aggregates. Bubbles often collect on the upstream side of such filters, effectively reducing the surface area of filter available to the fluid. Also, because gas may easily move across a filter, as dissolved gas, or as bubbles which may be smaller than the exclusion dimension of the filter, bubbles may accumulate on the opposite side of the filter as well.

Unwanted bubbles may also form in a microfluidic device by direct transfer of pressurized gas into the flow path of the microfluidic device. For example, when conventional flow cytometry sheath fluid reservoirs run out of fluid, or when the amount of fluid is low and the reservoir is not level, or when the sheath fluid reservoir is bumped, tipped, or shaken, pressurized gas can directly enter the flow path of the device. When pressurized gas enters the flow path of a microfluidic device directly, the bubbles can be much larger and in certain circumstances can interrupt of the flow of fluid all together, alter flow characteristics, or remain located in the flow path of the microfluidic device. If the microfluidic device or flow path is not disposable, a significant amount of time may be needed to dislodge or flush unwanted bubbles from the flow path.

Another problem related to the use of pressurized gas in contact with liquids to generate a fluid stream in microfluidic devices can be an increased concentration of oxygen in solution. For example, live sperm cells in the presence of media containing energy sources may exhibit a metabolic rate limited by the content of dissolved oxygen. During and after flow sorting of sperm cells it may be advantageous to have a viable but low metabolic rate. High concentrations of dissolved oxygen may be generated by equilibration of the sheath fluid with pressurized gases containing oxygen and its use may result in detrimentally high metabolic rates in sperm cells during flow analysis or flow sort processes.

A similar problem with the use of atmospheric gases or pressurized gases in contact with fluids to generate a fluid stream can be increased amounts of water introduced into anhydrous solvents or other water sensitive fluids used within microfluidic devices.

Another similar problem with the use of atmospheric gases or pressurized gases in contact with fluids to generate a fluid stream can be reaction of the certain gases with the fluid or the particles entrained in the fluid.

Another significant problem with conventional preparation of fluids for use with microfluidic devices or chromatographic systems can be that the available water quality or chemical solvent quality may be unacceptably low from which to make standardized solutions for certain applications. While there are numerous and varied methods to increase water quality, the cost of use may be unacceptably high when the source water contains a certain level of one or a plurality of materials, substances, or pathogens. This problem can be exacerbated with the use of specialized fluids for applications in basic research, clinical cell based therapy, or pharmaceutical production which may require fluids of higher quality with respect to precision of formulation, lot to lot consistency, and freedom from unwanted contaminating materials, particles, inorganic and organic substances, pathogens, chemicals, or the like. Particularly, with respect to fluids which are buffered or provide carbon sources to maintain cell function, high quality water may be essential to prevent, or reduce to acceptably low levels, the growth of pathogens.

A number of these problems are identified by U.S. Pat. No. 6,729,369 to Neas, which are addressed by preparing large volumes of sterile specialized fluids at a single geographic location at which high quality water and chemicals are available. Flexible walled vessels are then used for transporting the prepared sterile specialized fluids to the location where the fluids are used. Neas et al. does not, however, address the problem of establishing a pressurized fluid stream in the flow path of any microfluidic devices such as a flow cytometer, liquid chromatograph, or the like.

Another significant problem with conventional delivery of fluids to microfluidic devices can be cleanup, disposal of unused amounts of fluid, and sterilization of fluid reservoirs. Flow cytometers can consume between about 200 milliliters to about 800 milliliters of sheath fluid per hour, and are typically operated between about one hour and twenty four hours for a single procedure. The sheath fluid tanks or reservoirs typically contain between about five and about ten liters of sheath fluid, and if a procedure is interrupted or finished, it is often inconvenient to save the unused sheath fluid in the sheath fluid reservoir for use in the same procedure at a later date, because the sheath fluid tank may be needed for other procedures, or the sheath fluid may support the growth of microflora or microfauna, if stored. Even if the sheath fluid is stored, it may often be held at between 4-10° C., and must then be re-equilibrated to warm temperatures before further use.

In the broad consumer markets many products are distributed as containers of fluid which are opened for use, and accordingly, the fluids in the container begin to interact with atmosphere. With respect to certain fluids, interaction with atmosphere can be detrimental to the stability or consistency of the fluid. For example, paint or other surface coating products may begin to cure when exposed to atmosphere by moving toward equilibrium with the volume of atmosphere in the container. As such, an unused portion of paint in a container may form a thin layer of film. Another example may be free radical mediated rancidification of food oils such as olive oil, polyunsaturated vegetable oils, or the like, accelerated by molecular oxygen.

Many fluids are distributed in small pressurized containers which deliver the fluid through an orifice that causes the fluid to disperse when it exits the container. Common examples are cans of spray paint, hair spray, deodorant, insecticide, pesticide, herbicide, or the like. A disadvantage of the small pressurized containers is that there are a limited number of acceptable propellants which are both inert to reaction with contained fluid(s), and yet benign to the environment.

For larger scale application, these fluids are typically contained in reusable reservoirs which can be pressurized with a hand pumps or with air compressors. In addition to the problems above-discussed with respect to interaction of gas with the fluids, there are additional disadvantages related to the safety of cleaning large containers of the remaining fluids and the disposal of the remaining fluids.

Another significant problem associated with the use of microfluidic devices can be cleaning, conditioning or disinfecting of surfaces of conduits which define the flow path the microfluidic device. A disadvantage of conventional cleaning, conditioning or disinfecting compositions such as perchlorate, sodium chlorite, chlorine dioxide, chlorine gas, or oxygen can be that these compositions are strong oxidants which may damage or impair the surfaces which define the flow path of the microfluidic device. The use of these conventional cleaning, conditioning or disinfecting compositions may result in damage to the conduit surfaces which define the flow path, or alteration of the electrical charge of or on such conduit surfaces. In either event, these changes to the conduit surfaces can impair the subsequent performance of the microfluidic device with respect to analysis or separation of biological or non-biological particles. Another disadvantage of using strong oxidants for cleaning, conditioning, or disinfecting conduit surfaces can be that residual amounts remaining in the flow path of the microfluidic device can damage subsequently introduced biological particles through direct oxidation or through the generation of free radicals. Another disadvantage of certain conventional cleaning, conditioning, or disinfecting compositions can be that detergents added to assist in conduit surface cleaning can yield copious amounts of foam when exiting the flow path under pressure. Yet another disadvantage of conventional cleaning, conditioning or disinfecting compositions can be the formation of gas bubbles within the flow path of the microfluidic device. For example, when sodium chlorite is mixed with an acid chlorine dioxide can be produced, as shown by:

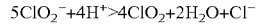

$$5ClO_2^- + 4H^+ > 4ClO_2 + 2H_2O + Cl^-$$

Chlorine dioxide can further decompose to generate chlorine gas and oxygen gas. Purging the flow path of microfluidic devices of the bubbles formed by these gases can take a substantial amount of time and failure to purge the flow path of these bubbles can result in the various problems above-described. With respect to the use of certain conventional cleaning, conditioning or disinfecting compositions which utilize sodium chlorite to produce chlorine and oxygen gas to condition or clean the flow path of flow cytometers, it appears that even several hours after purging the flow path of such cleaning compositions that performance of the flow cytometer may be less consistent due to bubble formation and nozzle clogging.

Another problem with conventional compositions used for cleaning, conditioning, or disinfecting can be that they pose a fire or explosion hazard. Solvents can pose a fire or explosion hazard, particularly at temperatures above the flash point. The flash point of a chemical is the lowest temperature at which a flame will propagate through the vapor of a combustible material to the liquid surface. It is determined by the vapor pressure of the liquid, since only when a sufficiently high vapor concentration is reached, can it support combustion. It should be noted that the source of ignition need not be an open flame, but could equally be, for example, the surface of a hot plate, or a steam pipe. Since average room temperature is about 25° C., and the flash points of methanol, ethanol, isopropanol, 2-butanol (SBA), acetone and 2-butanone (MEK) are 11° C., 9° C., 12° C., 24° C., −18° C. and −4° C., respectively all of these solvents can be fire hazards under certain room temperature conditions.

The instant invention provides fluid delivery devices and methods of fluid delivery as well as compositions and methods of using compositions to condition, cleaning or disinfect microfluidic devices.

III. SUMMARY OF THE INVENTION

Accordingly, a broad object of the invention can be to eliminate exposure of fluid(s) being delivered to the flow path of a microfluidic device or chromatography systems to external sources of contamination. One aspect of this object of the invention can be to isolate the fluids being delivered to the flow path of a microfluidic device from moving toward equilibrium with atmospheric gases, mixtures of gases, or partial pressures of gases whether at atmospheric pressure or at greater than atmospheric pressures. A second aspect of this object of the invention can be to isolate the fluids being delivered to the flow path of a microfluidic device from exposure to non-biological materials or surfaces, such as, pump surfaces, dust, cleaning compositions, or the like; or to biological substances or surfaces which may introduce pathogens, bacteria, viruses, spores, cells, proteins, nucleic acids, tissues, blood, semen, urine, feces, or the like. A third aspect of this object of the invention can be to maintain a sterile fluid to be delivered to the flow path of a microfluidic device.

Another broad object of the invention can be to provide a container which has a continuously adjustable volume with respect to the amount of fluid contained within so that a stream of the fluid can be delivered to a microfluidic device. One aspect of this object of the invention can be to provide a container which has continuously variable volume in response to pressure exerted on the exterior surface which allows the interior surface of the container to act upon the fluid contained within to generate a fluid stream at an outlet. A second aspect of this object of the invention can be to provide a flexible wall capable of withstanding a gas pressure of between about 70 pounds per square inch (psi) and 100 psi to generate a fluid stream in the flow path of a microfluidic device of about 25 psi to about 50 psi. Naturally, for certain applications the amount of pressure exerted on the flexible wall may be greater and for certain applications the amount of pressure may be less. A third aspect of this object of the invention can be to deliver from a container having continuously variable volume in response to the pressure exerted by an amount of gas or liquid a fluid stream to the flow path of a microfluidic device, such as a flow cytometer or liquid chromatograph, in which particles can be entrained for analysis, separation, purification, or otherwise manipulated as desired.

Another broad object of the invention can be to provide an improvement of, or retrofit to, conventional fluid reservoir technology which further includes a container which has a continuously adjustable volume with respect to the amount of fluid contained within so that a stream of the fluid can be delivered to a microfluidic device. One aspect of this object of the invention can be to retrofit conventional flow cytometer sheath fluid tanks to further include a container which has a continuously adjustable volume with respect to the amount of fluid contained within so that a stream of the fluid can be delivered to a flow cytometer. A second aspect of this object of the invention with respect to liquid chromatographs can be to retrofit conventional liquid phase reservoirs to further include a container which has a continuously adjustable volume with respect to the amount of fluid contained within so that a stream of the fluid can be delivered directly to the separation column or to the high pressure pump of the liquid chromatograph.

Another broad object of the invention can be to establish or maintain a desired concentration of a dissolved gas or gases in the fluid delivered in the flow path of a microfluidic device such that particles (whether biological or non-biological) are exposed to the concentration or level of gas(es) necessary or desired; or exposure of particles to certain unwanted gases, mixtures of gases, or partial pressures of gases, increased water content, or the like, can be avoided.

Another broad object of the invention can be to provide fluids which are prepared to conform to the specifications of a particular microfluidic device or method of using the microfluidic device and are transferred to a container having continuously variable volume in accordance with the invention. Such containers prepared at a first geographic location can then be shipped to numerous other geographic locations to maintain consistency of the fluids utilized by the microfluidic devices at each location.

Another broad object of the invention can be to provide a receptacle of substantially fixed configuration into which an amount of gas or liquid can be delivered to act on the surface of a container having variable volume to deliver fluid to the flow path of a microfluidic device. One aspect of this broad embodiment of the invention can be to provide a receptacle of substantially fixed configuration having a plurality of compartments allowing a plurality of fluids to be delivered simultaneously to one or more microfluidic devices or containers.

Another broad embodiment of the invention can be to provide a flow cytometer device or chromatographic system and methods of using such flow cytometer device or chromatographic system which utilize fluids separated from the surfaces of the sheath fluid tank, and the gases delivered to the sheath fluid tank.

Another broad object of the invention can be to provide fluids and methods of delivering fluids to the flow paths of microfluidic devices which are compatible with the isolation or purification of cells or other particles or substances for reintroduction into a human or animal. There are a significant number of concerns raised with respect to the prevention of transmission of infection or disease when cells, particles or substances are isolated by microfluidic devices. Infectious particles or other agents can vary in size from prions which can be a few tens of nanometers, to virus particles which may be a few hundreds of nanometers, to yeasts, fungus, molds and bacteria which can be several hundreds of nanometers to many micrometers in size. Once a sample of cells, particles or other substance is contaminated with such infectious particles, it can be very difficult to remove them. In some cases, agents such as preservatives or antibiotics are acceptable, but in most products being used in animals and humans, the governmental regulations requires use of production methods which can be validated to produce biological cells, particles, substances or chemicals free of all such adventitious infectious particles or agents. The instant invention facilitates the preparation, shipment, storage, handling, and use of validated sterile solutions (whether filtered or not) which are substantially free of adventitious particles or agents, which can be delivered under pressure to flow cytometers, flow cells, or other microfluidic devices or chromatographic systems to generate cells, particles or other substances free of infectious or other unwanted agents.

Specific examples of such treatments or therapies can be, the isolation of specific hematopoetic stem cells from bone marrow with the proceeding separation of cancerous or abnormal cells from normal cells, and the reinsertion of the non-cancerous or normal cells back into the bone marrow; the isolation of certain white blood cells or blood cancer cells and the modification of such cells with certain conjugates and adjuvants which allow the cells to be re-inserted (dead or alive) as a form of therapeutic vaccination; the isolation of very rare cells, such as fetal cells, from the blood, such as maternal blood, containing a very small number of said fetal cells, for the purpose of performing genetic analysis such as polymerase chain reaction (PCR), genotyping, or haplotyping of such fetal cells, with minimal genetic background from the much more abundant genetic content of the maternal blood cells; the isolation of cells such as sperm cells from the vaginal fluids for the purposes of analyzing genetic make-up of the sperm cells; the flow sorting of sperm cells of mammals to generate enriched X-chromosome bearing and Y-chromosome bearing populations of viable sperm or the flow sorting of sperm cells enriched for certain genetic traits for further use in assisted reproduction techniques such as in-vitro fertilization, intra-cytoplasmic sperm injection, artificial insemination, or the like.

Another broad object of the invention can be to provide a container which has a continuously variable volume with respect to an amount of conformable material contained within such that such conformable material such as: water, a fluid for a microfluidic device; a sheath fluid for flow cytometry; a food; a drink; a food ingredient; a drink ingredient; a liquid detergent; a liquid pesticide or herbicide; a pharmaceutical solvent such as rubbing alcohol; a toiletry product such as a shampoo, a body wash, a hairspray or hair gel; or the like, can be handled, delivered, flowed in the flow path of a conduit, or otherwise utilized with only the desired contact with the atmosphere or other partial pressures of gases and without release to the atmosphere or other partial pressures of gases, unless desired. One aspect of this embodiment is the provision of large variable volume containers which contain specialized concentrates which are useful in the processing industry which formulates and produces fluid products for consumers and may benefit from new methods for accurate and clean delivery of fluid products, at controlled amounts, into the products they are compounding.

Another broad object of the invention can be to provide compositions and methods of using such compositions for cleaning, conditioning, or disinfecting to remove, reduce in numbers, or eliminate live organisms such as bacteria, yeast, viruses, viable spores, or other live cells or particles; biological materials such as cell components, proteins, nucleic acids, fatty deposits, or the like; or non-biological materials such as salts, mineral deposits, precipitates, or the like. With respect to certain compositions or fluids encompassed by the invention, these compositions can have specific application for the cleaning, conditioning, or decontamination of the conduit surfaces which define the flow paths of various types of microfluidic devices including liquid chromatographs, peptide and nucleic acid synthesizers, flow cytometers, or the like.

Another broad object of the invention can be to provide compositions which contain an aqueous component useful for the solvation, removal, or reduction of hydrophilic materials, salts, or the like, while further containing a miscible non-aqueous component, such as an alcohol, useful in killing, deactivating, disrupting, or suspending living biological particles, components of living biological particles, and other biological materials as described above.

Another broad object of the invention can be to further provide compositions as describe above, further including a ketone component which further contributes to the effective killing, deactivating, disrupting, or suspending of living biological particles, components of living biological particles, and other biological materials.

Another broad object of the invention can be to provide compositions and methods of using such compositions to clean, condition, or decontaminate the flow path of a flow cytometer. As discussed above, an advantage of utilizing the compositions encompassed by the invention can be the decontamination of the flow path of the flow cytometer of living organisms and biological materials while being useful in the solvation or reduction of non-biological materials. With respect to certain of such compositions, an advantage can be that the composition does not damage or impair the surfaces of the conduit which define the flow path of the flow cytometer. Another advantage of such compositions can be that they do not alter the electrical charge of the surfaces of the conduits which define the flow path of the flow cytometer in a manner which substantially affects the performance of the flow cytometer. Another advantage of such compositions can be a reduction in the generation of foam or bubbles within the flow path of the flow cytometer or upon exiting the nozzle of the flow cytometer. Yet another advantage of such compositions can be a reduction in the time to purge the composition from the flow path of the flow cytometer and re-equilibration of flow cytometer to a consistent performance standard.

Another broad object of the invention can be to provide compositions as described above to clean, condition, or decontaminate the flow path of a microfluidic instrument which can be handled and delivered to the flow path of such microfluidic instrument from the various embodiments of a pressure regulated continuously variable volume container as described herein.

Another broad object of the invention can be to provide compositions for cleaning, conditioning, or disinfection of the flow path of microfluidic devices which exhibit low fire or explosion risk. Compositions encompassed by the invention provide combinations of water, alcohol, and ketone which can provide cleaners, conditioners, or disinfectants which exhibit higher flash points, and therefore less fire and explosion hazard as compared to methanol, ethanol, isopropanol, 2-butanol (SBA), acetone or 2-butanone (MEK), individually.

Naturally, further objects of the invention are disclosed throughout other areas of the specification, drawings, and claims.

III. A BRIEF DESCRIPTION OF THE DRAWINGS

FIG. 1A shows an embodiment of the invention which provides a pressure regulated variable volume container which delivers a fluid stream in response to an amount of gas acting on the exterior surface.

FIG. 1B shows a cross section through the flexible wall of an embodiment of the pressure regulated variable volume container.

FIG. 1C shows a cross section through the flexible wall of alternate embodiment of the pressure regulated variable volume container.

FIG. 1D shows a cross section through the flexible wall of second alternate embodiment of the pressure regulated variable volume container.

FIG. 1E shows a cross section through the flexible wall of third alternate embodiment of the pressure regulated variable volume container.

FIG. 2A shows a conventional sheath fluid tank for the delivery of sheath fluid(s) to a flow cytometer.

FIG. 2B shows an embodiment of the invention for the delivery of sheath fluid(s) to a flow cytometer in which a conventional sheath fluid tank is retrofitted to receive an amount of gas which acts upon the exterior surface of a variable volume container.

FIG. 2C shows an alternate embodiment of the invention for the delivery of sheath fluid(s) to a flow cytometer in which a conventional sheath fluid tank is retrofitted to receive an amount of gas which acts upon the exterior surface of a variable volume container.

FIG. 3A shows an embodiment of the invention in which a receptacle of substantially fixed configuration receives an amount of gas which acts upon the exterior surface of a variable volume container.

FIG. 3B shows an alternate embodiment of the invention in which a receptacle of substantially fixed configuration receives an amount of gas which acts upon the exterior surface of a variable volume container.

FIG. 6 shows a bivariate plot of sperm cells entrained in a fluid stream generated in accordance with the invention differentiated into X-chromosome bearing and Y-chromosome bearing populations.

Figure 9:
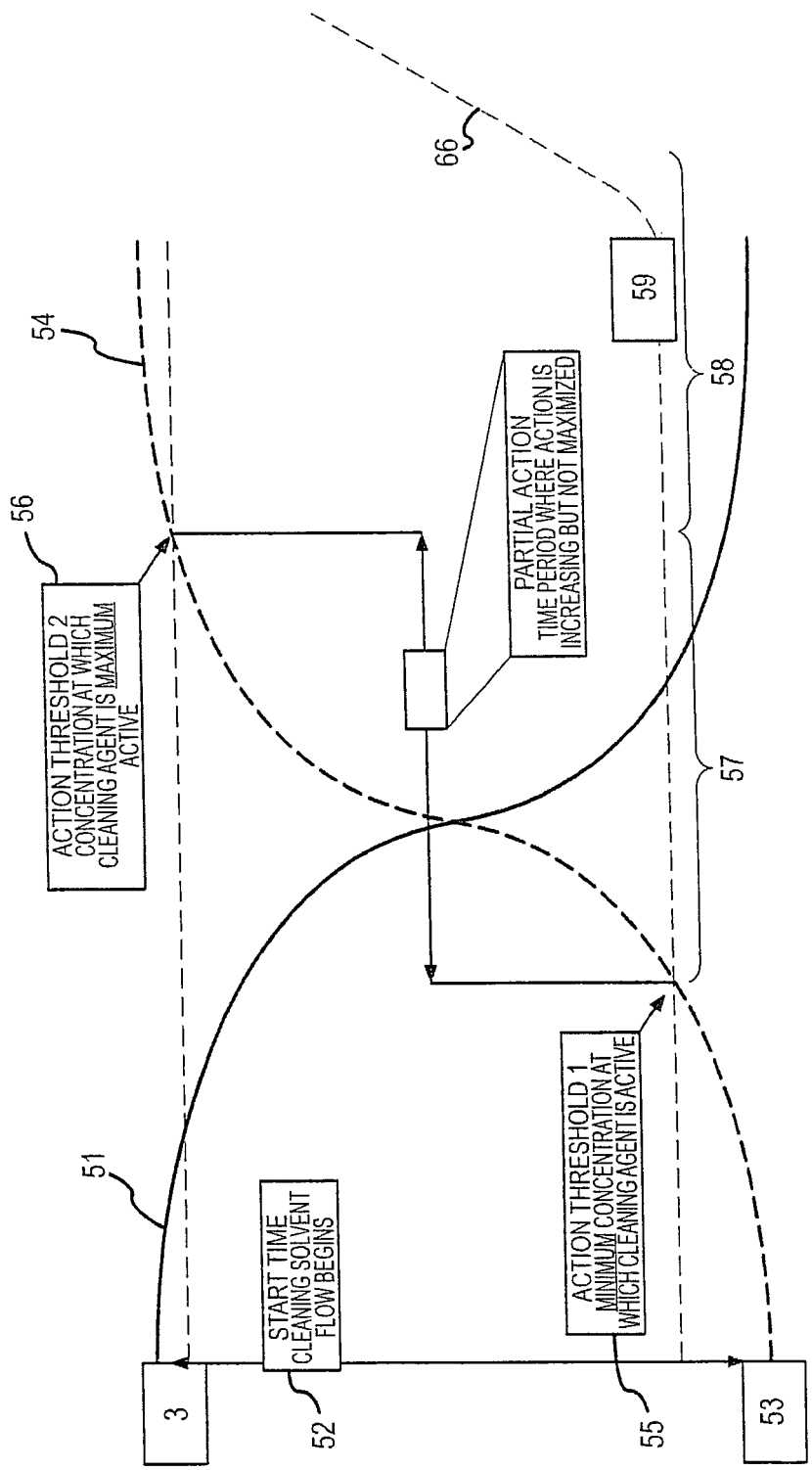
Figure 10C:
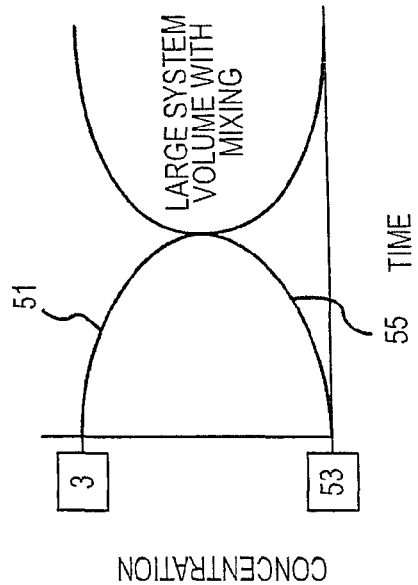
Figure 10B:
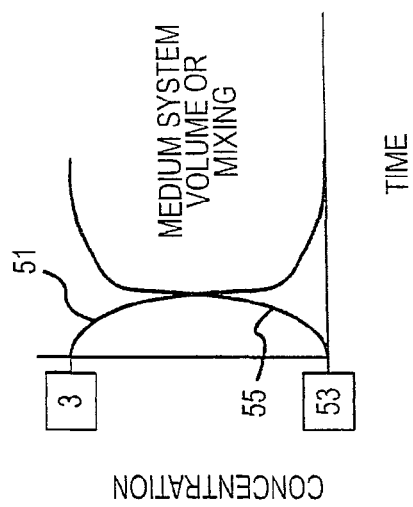
Figure 10A:
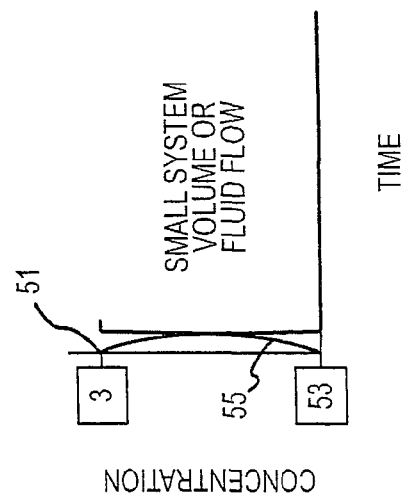

FIG. 9 provides a graph which shows the replacement of a first fluid within the flow path of a microfluidic device with a second fluid being an embodiment of the invention FIG. 10A provides a graph which shows the fluid dynamics during the replacement of a first fluid within the flow path of a microfluidic instrument to a second fluid being an embodiment of the invention.

FIG. 10B provides a graph which shows the fluid dynamics during the replacement of a first fluid within the flow path of a microfluidic instrument to a second fluid being an embodiment of the invention.

FIG. 10C provides a graph which shows the fluid dynamics during the replacement of a first fluid within the flow path of a microfluidic instrument to a second fluid being an embodiment of the invention.

Figure 11:
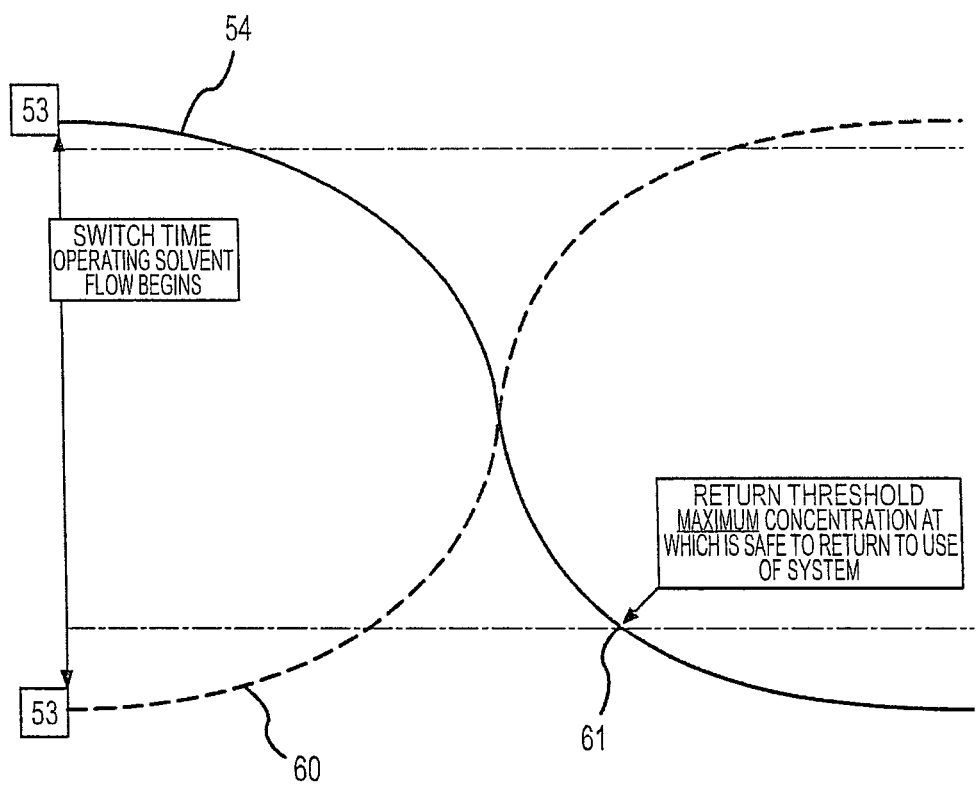

FIG. 11 provides a graph which shows the replacement of a second fluid being an embodiment of the invention within the flow path of a microfluidic device with a third fluid to return the microfluidic device to an operating condition.

Figure 12:
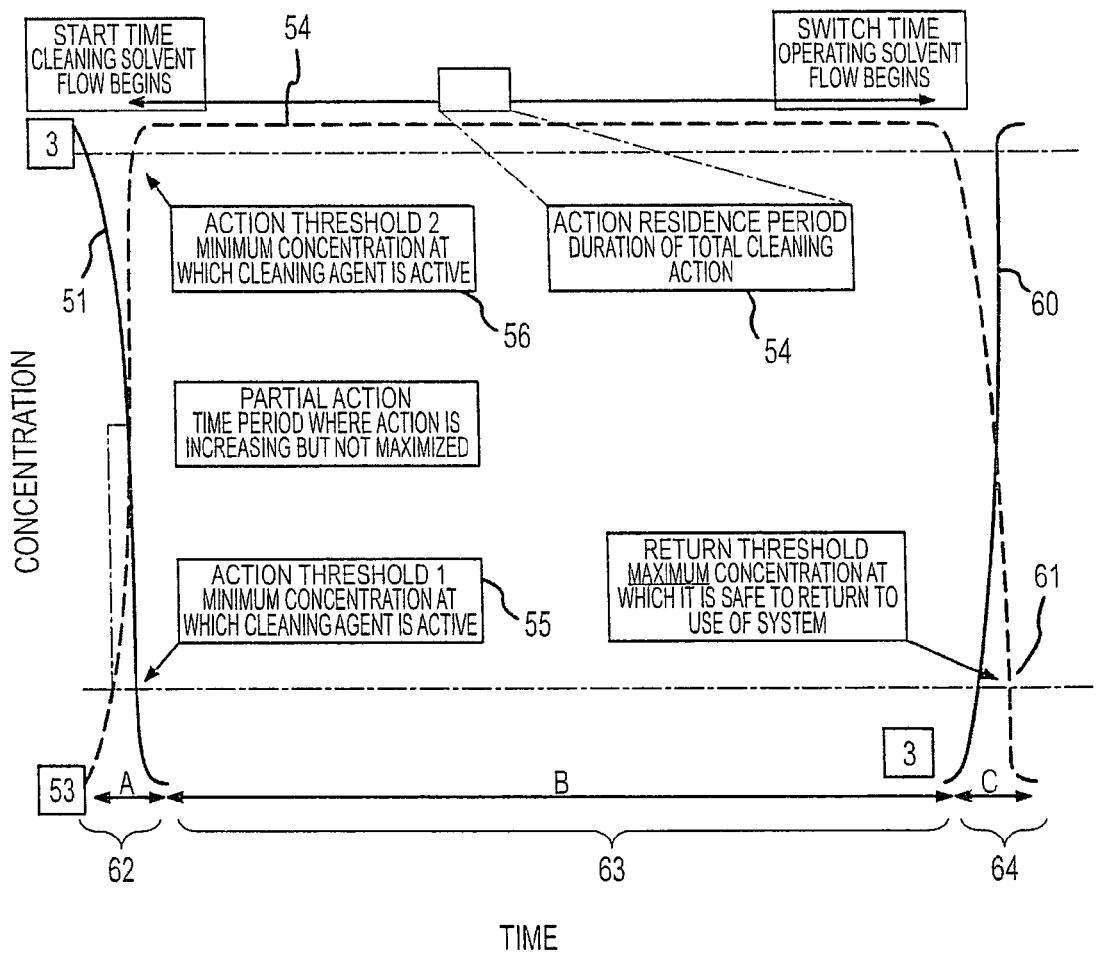

FIG. 12 provides a graph which shows the concentration of three fluids within the flow path of a microfluidic device while using a three step process in accordance with the invention to clean, condition, or disinfect the flow path of the microfluidic device.

Figure 13:
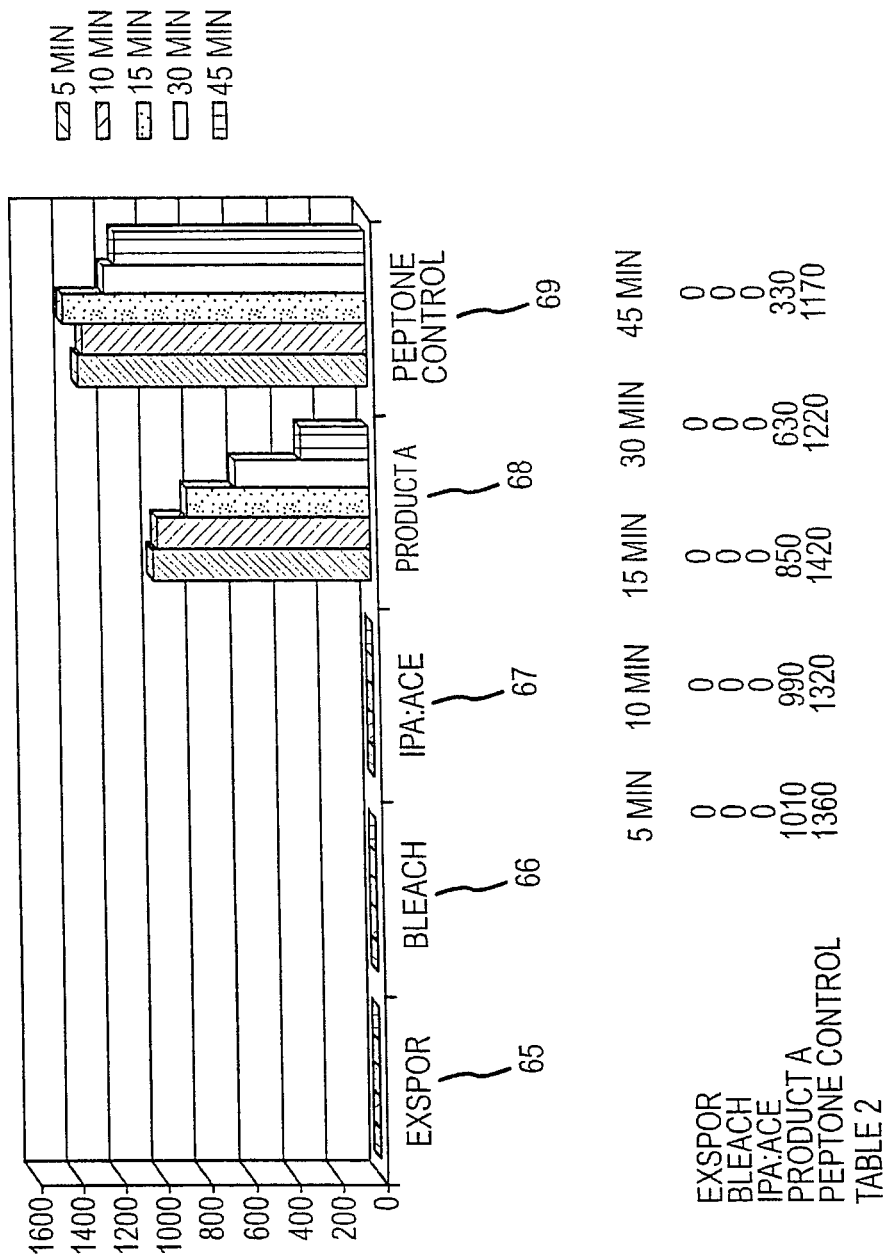

FIG. 13 provides a table and a graph of the results of a challenge test using three different conventional compositions and an embodiment of the invention against *E. coli* compared to a control composition.

Figure 14:
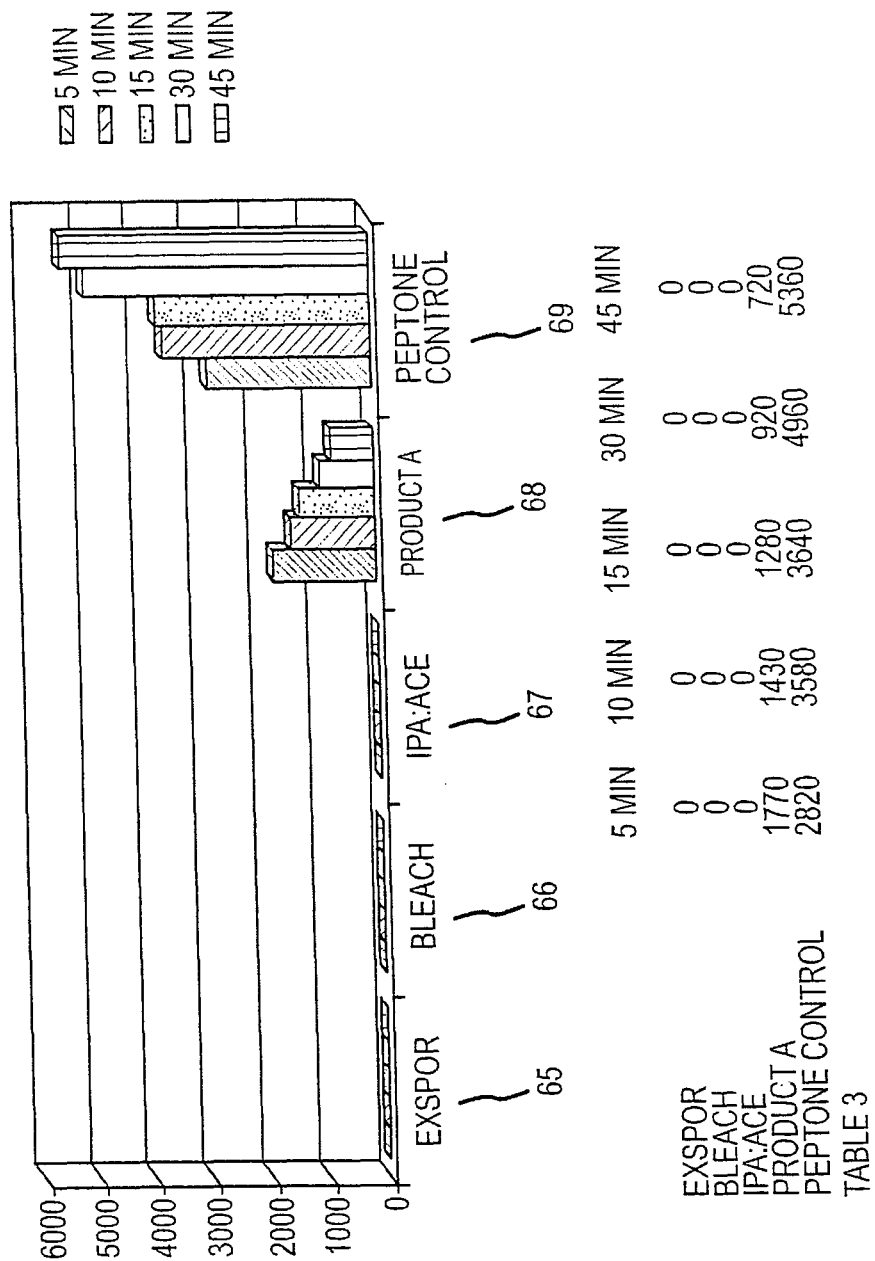

FIG. 14 provides a table and a graph of the results of a challenge test using three different conventional compositions and an embodiment of the invention against *P. aeruginosa* compared to a control composition.

V. DETAILED DESCRIPTION OF THE PREFERRED EMBODIMENTS

Generally, an amount of fluid located within a variable volume container having a flexible wall which acts upon the amount of fluid in response to gas pressure exerted on the exterior surface to generate a fluid stream in the flow path of a conduit. Specifically, compositions which can be located within such a variable volume container, or used without such variable volume container, useful in cleaning, conditioning, or decontaminating surfaces within the flow path of a microfluidic device.

Now referring primarily to FIG. 1, an embodiment of the invention can provide a variable volume container (1) having a flexible wall (2) which can act on an amount of fluid (3) within the variable volume container (1) in response to an amount of pressure (4) exerted on the exterior surface (5) of the flexible wall (2) by an amount of gas (6). The amount of pressure (4) exerted on the exterior surface (5) of flexible wall (2) can continuously adjust the volume of the variable volume container (1) to act on the amount of fluid (3) to generate a fluid stream (7) (whether of continuous flow or of discontinuous flow) in the flow path of a conduit (8). As to certain embodiments of the invention, the variable volume container (1) can in part be of substantially rigid configuration and in part a flexible wall (2). That portion of the variable volume container (1) which provides the flexible wall (2) can act on the amount of fluid (3) within the variable volume container (1) in response to the amount of pressure (4) exerted on the exterior surface (5) of the flexible wall by the amount of gas (6) to generate a fluid stream (7).

The fluid (3) within the variable volume container (1) broadly encompasses without limitation any fluid, liquid, composition, mixture, phase, product, or other material flowable in the flow path of the conduit (8) by continuous adjustment of the volume of the variable volume container (1) in response to the amount of pressure (4) exerted on exterior surface (5) of the flexible wall (2). The numerous and varied fluids flowable in the flow path of the conduit (8) (the flow path of the conduit includes numerous and varied configurations corresponding to the broad range of applications for the invention and without limitation includes microfluidic flow paths or conduits which typically have an internal diameter of about one millimeter or less) includes without limitation: water, a solvent, a solution, a buffered solution, a liquid chromatography solution, a fluid in which biological particles can be entrained, a fluid in which non-biological particles can be entrained, a fluid in which cells can be analyzed, a fluid in which sperm cells can be analyzed, a fluid in which sperm cells can be separated into Y-chromosome bearing and X-chromosome bearing populations, a flow cytometry sheath fluid, a flow cytometry sheath fluid in which non-biological particles can be entrained, a flow cytometry sheath fluid in which biological particles can be entrained, a flow cytometry sheath fluid in which cells are entrained, a flow cytometry sheath fluid in which spermatozoa can be entrained, a flow cytometry sheath fluid in which stained spermatozoa can be entrained, paint, pesticides, pastes, adhesives, organic solvents, pesticides, food products, beverages, and various permutations and combinations thereof and specifically includes the compositions described below for the conditioning, disinfection, and cleaning of the flow paths established by conduits of microfluidic devices such as liquid chromatographs, flow cytometers, or the like.

Now referring primarily to FIG. 1B, the variable volume container (1) can provide a flexible wall (2) on which the amount of gas (6) exerts an amount pressure (4). The flexible wall (2) can comprise a layer of material (9) which has sufficient flexibility to adjust volume of the variable volume container (1) in response to the amount of pressure (4) exerted by the amount of gas (6) on the exterior surface (5). The layer of material (9) can be selected to provide an interior surface (10) compatible with the fluid (3) contained within the variable volume container (1) and to provide an exterior surface (5) compatible with the amount gas (6) which exerts the amount of pressure (4) thereon. With respect to certain embodiments of the invention, the layer of the material can further be selected to prevent or minimize the transfer of materials leachable or transferable from the layer of material (9) to the fluid (3) held by the variable volume container (1). The layer of material (9) can further be selected to prevent or minimize the transfer the amount of gas (6) through the layer of material (9) to the fluid held by the variable volume container (1). Without limiting the numerous and varied materials that can be used in accordance with the invention, preferred embodiments of the invention can utilize a layer of material (9) such as a polypropylene, a polyethylene, a nylon, a fluorocarbon, a styrene, a polycarbonate, a metal foil, a laminated paper, a biodegradable polymer, a waxed paper, or bonded layers thereof in various permutations and combinations. The layer of material (9) can include a coat of material, such as an oxygen barrier, a water barrier, alternate layers of a surface filling polymer and a ceramic (for example BARIX, Vitex Systems, Inc. 3047 Orchard Parkway, San Jose, Calif., 95134 USA), or the like.

Now referring primarily to FIG. 1C, as to other embodiments of the invention the flexible wall (2) can comprise two layers of material. The first layer (11) which establishes the exterior surface (5) compatible to the amount of gas (6) which exerts a pressure (4) on the flexible wall (2) and a second layer (12) providing an interior surface (10) compatible with the fluid (3) within the variable volume container (1). The first layer (11) can be selected from materials such as a polypropylene, a polyethylene, a fluorocarbon, a styrene, a polycarbonate, a Mylar® film, an oxygen barrier, a water barrier, or the like. The second layer (12) can be selected from the same or a different material then the first layer (11) such as a polypropylene, a polyethylene, a fluorocarbon, a styrene, a polycarbonate, a water barrier, or oxygen barrier (for example Barix), or the like. Either or both of the first layer (11) or the second layer (12) can be further include a reinforcement element (48) such as individual fibers, threads, strands, a net, web, or the like, which can be made of a reinforcement material such as a nylon, a cotton, a carbon fiber, a metal strand, a plastic strand, or the like.

As to certain embodiments of the invention, the first layer (11) and the second layer (12) of the flexible wall (2) can slidably engage, while as to other embodiments of the invention the first layer (11) and the second layer (12) can be fixedly engaged. Fixed engagement between the first layer (11) and the second layer (12) can be generated by the use of an adhesive layer (13), or other type of layer, or other process which induces a surface of the first layer (11) and a surface of the second layer (12) to adhere to each other.

Now referring primarily to FIG. 1D, as to other particular embodiments of the invention, a gas collection element (14) can be interposed between the first layer (11) and the second layer (12). As to these embodiments of the invention, the amount of gas (6) which exerts an amount of pressure (4) on the exterior surface (5) of the variable volume container (1) collects in the gas collection element (14) and exerts an amount of pressure (4) on the second layer (12) which acts on the liquid (3) contained within the variable volume container (1) to generate the fluid stream (7) in the flow path of the conduit (8). The first layer (11) has a configuration which contains the amount of gas (6) within gas collection element (14) and allows adjustment of the volume or pressure (or both) of the amount of gas (6) within the gas collection element (14) to the necessary or desired amount. As to these embodiments of the invention, in which the first layer (11) does not have to function as part of a flexible wall (2) of the variable volume container (1), the first layer (11) can have a substantially fixed configuration formed from a material such as a plastic, a fiberglass, a glass, a metal, a steel, a polycarbonate, an acrylic, a polypropylene, a vinyl, a fluorocarbon, a carbon fiber, or the like.

Now referring primarily to FIG. 1E, other embodiments of the invention can further include a flexible wall (2) having at least one intermediate layer (15) located between the first layer (11) and the second layer (12). The at least one intermediate layer (15) can be can be selected from a material such as a polypropylene, a polyethylene, a fluorocarbon, a styrene, a polycarbonate, a MYLAR® film, a ceramic layer, an oxygen barrier (or other gas), a water barrier, or the like. Additional embodiments of the invention can further provide the gas collection element (14) (similar to FIG. 1D) interposed between the first layer (11) and the at least one intermediate layer (15), or as to other particular embodiments of the invention the gas collection element (14) (similar to FIG. 1D) can be interposed between the second layer (12) and the at least one intermediate layer (15). Where the gas collection element (14) is interposed between the first layer (11) and the at least one intermediate layer (15), the first layer (11) can be of substantially fixed configuration as above-described. In those embodiments of the invention in which the gas collection element (14) is interposed between the second layer (12) and the at least one intermediate layer (15), either of the first layer (11) or the at least one intermediate layer (15), or both, can have a substantially fixed configuration, while the second layer (12) provides sufficient flexibility to allow the variable volume container (1) to continuously adjust volume in response to the amount of pressure (4) exerted by the amount of gas (6) on the flexible wall (2). As to those embodiments of the invention, in which the liquid (3) engages the interior surface (10) of the second layer (12) and the amount of gas (6) exerts an amount of pressure (4) on the exterior surface (5) of the first layer (11), then the first layer (11), the intermediate layer (15) and the second layer (12) can have sufficient flexibility to allow variable adjustable volume of the container (1) whether the surfaces of the layers have slideable or fixed engagement.

The amount of gas (6) which exerts an amount of pressure (4) on the exterior surface (5) of the flexible wall (2) to provide a continuously adjustable variable volume container (1) to act on the fluid (3) contained within can be any type or kind of gas (6) compatible with the exterior surface (5) of the flexible wall (2) on which it acts, such as, an atmosphere, a mixture of gases, a mixture of gases having selected partial pressures, a purified gas, a filtered gas, a conditioned gas, or the like. As to alternate embodiments of the invention, the amount of gas (6) can be replaced with an amount of flowable material capable of acting upon the exterior surface (5) of the flexible wall (2) to adjust the volume of the container (1), such as water, oil, or a solution.

With respect to certain embodiments of the invention, the gas (6) can exert an amount of pressure (4) on the exterior surface (5) of the flexible wall (2) of between 1 pound per square inch (psi) to about 500 pounds per square inch (psi). As to other embodiments of the invention utilized for flow cytometry applications, the amount of gas (6) can exert a pressure on the exterior surface (5) of the flexible wall (2) of between about 10 psi and about 200 psi. Alternately, the amount of gas (6) whether within the gas collection element (14), or otherwise, can be adjusted to generate a sufficient amount of pressure (4) on the exterior surface (5) of the flexible wall (2) of the variable volume container (1) to generate a fluid stream (7) within the flow path of a conduit (8) of a microfluidic device (16) having a fluid pressure of between 10 psi and about 200 psi, or a fluid pressure sufficient to generate a fluid stream (7) within the flow path of the conduit (8) having a velocity sufficient to entrain particles for a particular type or kind of application, analysis, differentiation, or separation.

Again referring primarily to FIG. 1A, particular embodiments of the invention can further include fluid pressure generator (17), such as a peristaltic pump, piston pump, or the like to generate sufficient pressure for certain microfluidic applications, or other applications, in the range of between about 100 psi and about 5000 psi. One illustrative embodiment of the invention, provides a microfluidic device (16) configured as a high pressure liquid chromatograph (HPLC) having a fluid pressure generator (17) which increases fluid pressure within the conduit (8) to between about 100 psi and about 3000 psi for applications such as normal phase or reverse phase liquid chromatography.

Now referring primarily to FIG. 2A, a conventional substantially cylindrical sheath fluid tank (18) (or other configuration of sheath fluid tank) can have an aperture element (19). The aperture element (19) of the sheath fluid tank (18) can be configured to mate with a removably sealable closure (20) which can further include a closure securement element (21) to secure the removably sealable closure (20). Alternate embodiments of the closure securement element (21) can include, as examples, mated spiral threads on the removable sealable closure (20) and the sheath fluid tank (18), spiral threaded rods connected to the sheath fluid tank which mate with spirally threaded hardware which operationally apply pressure to the removably sealable closure (20), straps, catches, or the like.

A gas inlet element (22) allows delivery of an amount of gas (6) (various types and kinds of gas(es) as above-described) to the interior of the sheath fluid tank (18). In conventional applications, an amount of fluid (3) is contained by the sheath fluid tank (18) and the amount of gas (6) delivered to the interior of the sheath fluid tank (18) exerts an amount of pressure (4) on the surface of the fluid (3). A portion of the fluid (3) under pressure flows through the fluid outlet element (23) to be delivered as a fluid stream (7) in the flow path of a flow cytometer (24) (or other microfluidic device). A pressure adjustment element (25) (such as a pressure relief valve) can allow for adjustment of the amount of pressure within the sheath fluid tank (18).

Now referring primarily to FIG. 2B, a conventional sheath fluid tank (18) (or similar fluid tank) can be adapted to operate in accordance with the invention. A variable volume container (1) having a flexible wall (2) can contain an amount of fluid (3) (sheath fluid for flow cytometry applications). The variable volume container (1) containing the fluid (3) can be located inside of the conventional sheath fluid tank (18) by transfer through the aperture element (19). A conduit (8) provides a flow path between the variable volume container (1) and the fluid outlet element (23). A coupler element (26) may be required to connect the conduit (8) to the fluid outlet element (23) of the sheath fluid tank (18). The coupler element can in certain instances comprise mated spirally threaded hardware which operates to compress a ferrule against a seat to seal the flow path within the conduit (8) from leaking fluid. Naturally, a variety of hardware can be used as the coupler element (26) to provide a continuous flow path to the fluid outlet element (23).

Now referring primarily to FIG. 2C, as to certain embodiments of the invention the variable volume container (1) can be enclosed by a second layer (12) of substantially fixed configuration as discussed above formed from a material such as a plastic, a fiberglass, a glass, a metal, a steel, a polycarbonate, an acrylic, a polypropylene, a vinyl, a fluorocarbon, a carbon fiber, a paperboard, a cardboard, or the like. The second layer can be sufficiently perforated or permeable to an amount of gas (6) to allow an amount of pressure (4) to be exerted on the exterior surface (5) of the flexible wall (2) to act upon the amount of liquid (3) or sheath fluid contained within to generate a fluid stream (7) within the flow path of the conduit (8).

Now referring primarily to FIG. 3A, certain embodiments of the invention can provide a receptacle (27) of substantially fixed configuration (rectangular as shown by FIG. 3A or otherwise as desired) in which one or more variable volume container(s) (1) having a flexible wall (2) can be located. The receptacle (27) may be mounted on a base (28) which orients the receptacle (27) relative to a support surface (29) (for example, angled as shown by FIG. 3A or substantially perpendicular to the support surface (29) as shown by FIG. 3B) which can facilitate flow of the fluid (3) within the variable volume container (1) toward the conduit (8) which communicates with the fluid outlet element (23). The receptacle (27) of substantially fixed configuration can be made from a material such as a plastic, a fiberglass, a glass, a metal, a steel, a polycarbonate, an acrylic, a polypropylene, a vinyl, a fluorocarbon, a carbon fiber, or the like. A portion or the entirety of the receptacle (27) can be made from a material which allows visual observation of the variable volume container (1) and the fluid (3) within the variable volume container (1). The receptacle (27) can further include a gas inlet element (22) through which an amount of gas (6) can be introduced into the gas collection element (14) between the interior surface of the receptacle (27) and the exterior surface (5) of the variable volume container (1). A pressure adjustment element (25) can be further included to maintain the necessary or desired amount of gas pressure (4) exerted on the exterior surface (5) of the variable volume container (1).

Figure 4A:
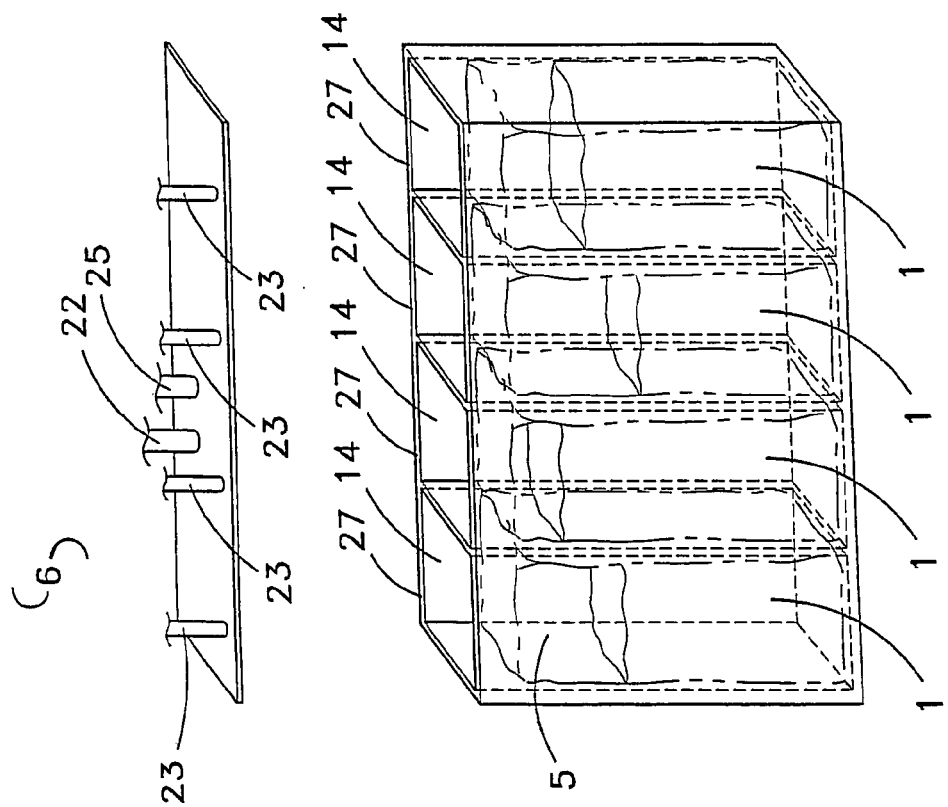
FIG. 4A shows an embodiment of the invention in which a plurality of receptacles each receive an amount of gas which acts upon the exterior surface of a variable volume container to generate a plurality of fluid streams.
Figure 4B:
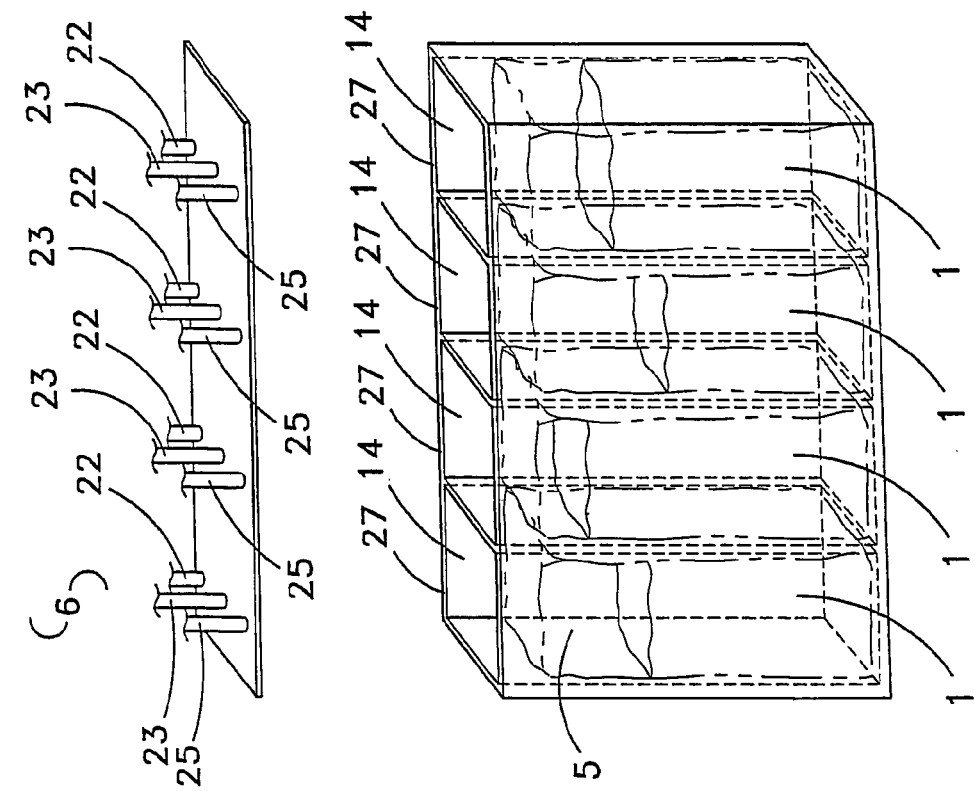
FIG. 4B shows an alternate embodiment of the invention in which a plurality of receptacles each receive an amount of gas which acts upon the exterior surface of a variable volume container to generate a plurality of fluid streams.

Now referring primarily to FIG. 4A, certain embodiments of the invention can include a plurality of receptacles (27), individually discrete or as a single integral piece (as shown by FIGS. 4A and 4B) providing a corresponding plurality of gas collection elements (14). FIG. 4A illustrates that each of the plurality of gas collection elements (14) can provide independent gas inlet elements (22), fluid outlet elements (23), and pressure adjustment elements (25) to allow each of the plurality of receptacle (27) to be utilized independent of the other receptacles (27). In this configuration of the invention, an amount of gas (6) can be delivered to each gas collection element (14) to establish an amount of pressure (4) on the exterior surface (5) of the flexible wall (2) of the variable volume container (1) located inside the individual receptacle (27). Accordingly, an amount of the fluid (3) contained in each of the variable volume containers (1) can be delivered to the fluid outlet element (23) from each receptacle (27). The fluid flow rate from each variable volume container (1) can be adjusted to be substantially the same or variably adjusted between receptacles (27).

Now referring primarily to FIG. 4B, alternate embodiments of the invention can provide a single gas inlet element (22) to deliver an amount of gas (6) to all the gas collection elements (14) to establish a substantially similar amount of gas pressure (4) on the exterior surface (5) of the flexible wall (2) of each of the plurality of variable volume containers (1) in the corresponding each of the plurality of receptacles (27) which can be adjusted by a single pressure adjustment element (25). Each receptacle can further provide a fluid outlet element (23) through which a fluid stream (7) can flow to the flow path of a microfluidic device (16) (similar to that shown in FIG. 1A).

Figure 5:
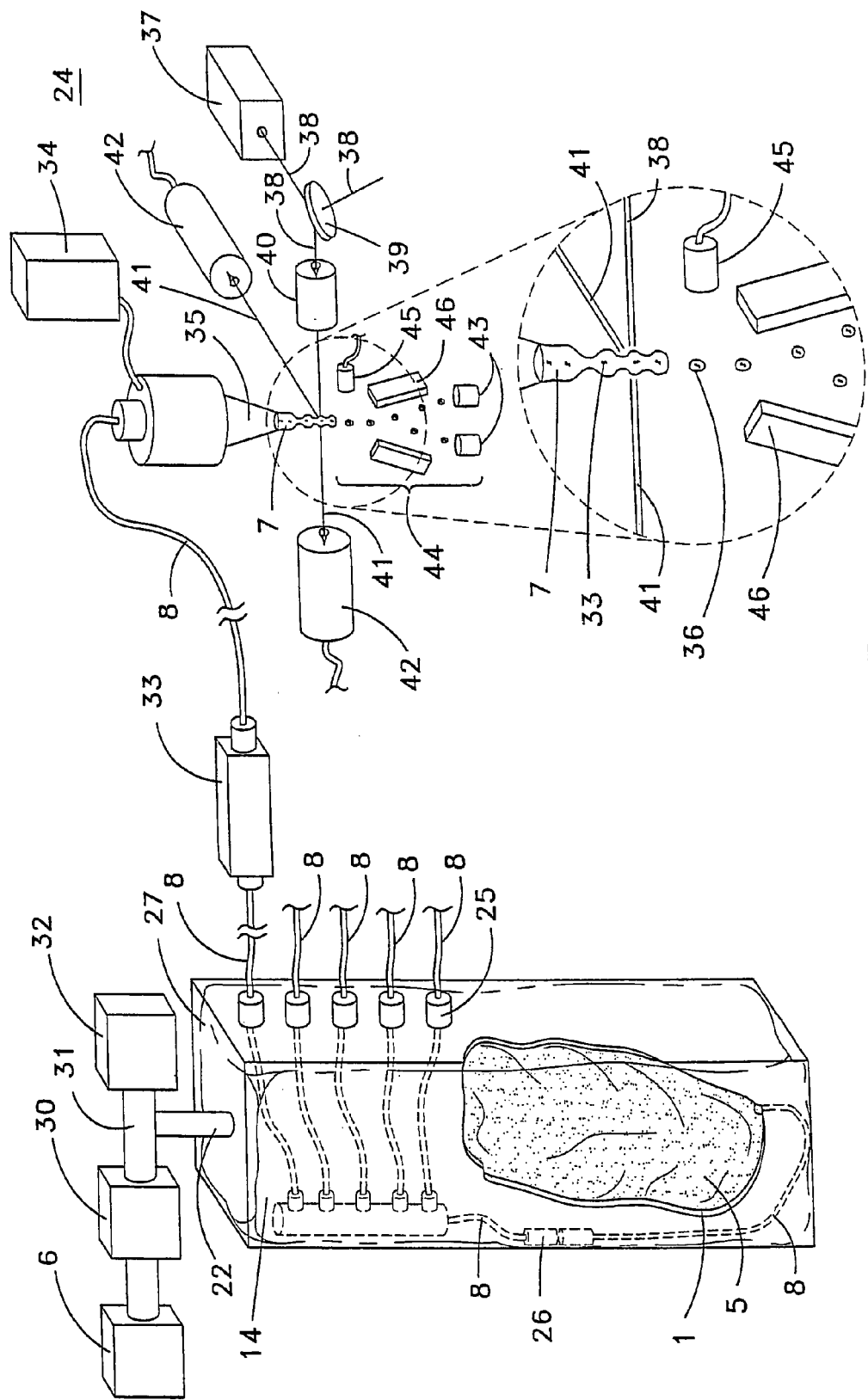
FIG. 5 shows a flow cytometer embodiment of the invention in which a fluid stream can be generated in the flow path of the flow cytometer from a variable volume container acted upon by an amount of gas.

Now referring primarily to FIG. 5, a generic microfluidics device in accordance with the invention is illustrated. An amount of gas (6) can be delivered with a pressure differential generator (30) such as a tank of pressurized gas, a gas compressor, or the like, to one or more gas inlet elements (22) of the receptacle(s) (27) through a gas transfer conduit (31). A pressure regulator (32) can be further included to regulate the pressure of the amount of gas (6) in the gas transfer conduit (31). The amount of gas (6) transfers from the gas inlet element (22) to a gas collection element (14) inside the receptacle (27) which can have a substantially fixed configuration as shown, or alternately described herein. At least one variable volume container (1) as above-described can be located inside the receptacle (27).

The amount of gas (6) within the gas collection element (14) acts upon the exterior surface (5) of the at least one variable volume container (1) located within the receptacle (27) to generate a fluid stream (7) at the fluid outlet element (25) which can be transferred within one or a plurality of conduits (8). The conduits (8) can have substantially the same internal diameter or varying internal diameters. The conduit (8) can further include a fluid conditioning element (33) such as a fluid filter, a gas scrubber, or a fluid pressure regulator, fluid pressure generator, such as a pump, or various permutations or combinations thereof. The conduit (8) can be connected to the flow path of a microfluidics device (24), such as a flow cytometer as shown in FIG. 5, or other microfluidic device, such as a fluid distribution device which transfers liquid(s) to and between locations on a liquid containment element such as plates having a plurality of wells, the surface of slides, cuvettes, channels, or other containment features.

As to the flow cytometer embodiment of the invention shown in FIG. 5, the fluid stream (7) can entrain particles (33)

(as described above) delivered from a particle source (34). The fluid stream (7) having particles (33) entrained can be oscillated by a nozzle (35) to generate a plurality of droplets (36) below the nozzle (35). Each of the plurality of droplets (36) can entrain an individual particle (33). An illumination source (37), such as a laser, can emit a beam of light (38), or a plurality of beams of light can be generated by utilizing a beam splitting element (39) (or by utilizing a plurality of illumination sources (37)), which can be focused through an optical element (40) incident upon the particle (33) entrained in the fluid stream (7) below the nozzle (35), either as a single beam of light or a plurality of beams of light, whether at the same or different wave lengths. As to some embodiments of the invention, characteristics of the beam of light (38) can be altered by incidence upon the particle (33) within the fluid stream (7), and as to other embodiments of the invention the particle (or ligands, fluorescent materials, or the like, attached to the particle) can generate an emission (41). The beam(s) of light having altered characteristics or the emission (41) can be received by a single or a plurality of detectors (42) which can generate a signal for analysis to differentiate the particles (33) entrained in the droplets (36) based upon one or a plurality of particle characteristics. The differentiated particles can be separated based upon the presence or absence of one or a plurality of particle characteristics into individual collection elements (43). The separation device (44) can include a droplet charge generator (45) which induces a positive or negative charge in each droplet (36) and a droplet deflector (46) which acts upon the charged droplets to establish a trajectory to the proper collection element (43).

Now referring primarily to FIG. 6, a bivariate plot generated during the flow sort of spermatozoa into X-chromosome bearing and Y-chromosome bearing populations in accordance with the invention is shown. The bivariate plot shows that a mixture of X-chromosome bearing sperm cells and Y-chromosome bearing sperm cells can be resolved into first X-chromosome bearing population (49) and second Y-chromosome bearing population (50). Provision of the bivariate plot is not intended to be limiting with respect to the numerous and varied applications of the invention. Rather, the bivariate plot is intended to be illustrative of the broad range of applications in which the invention can be utilized.

Figure 7:
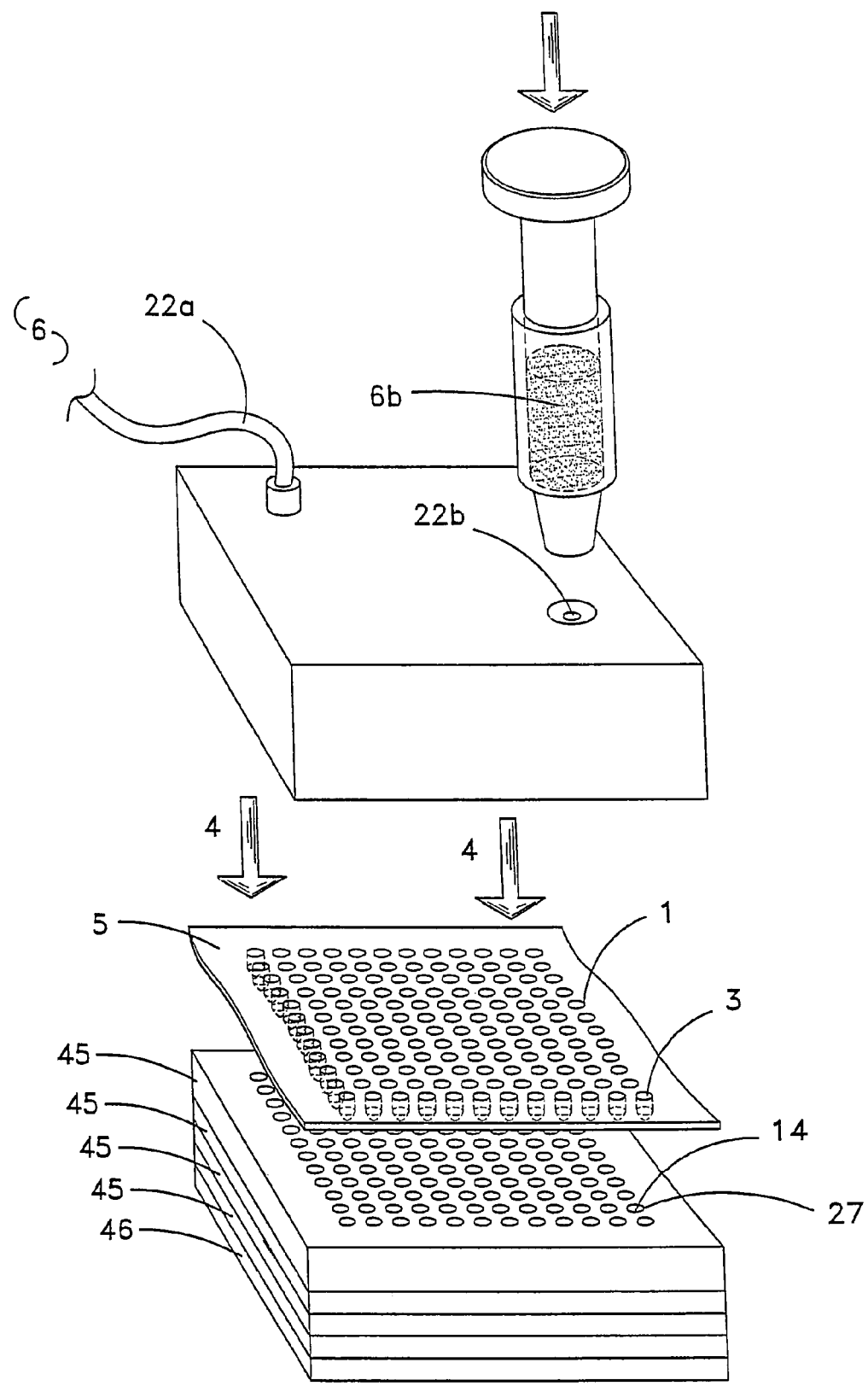
FIG. 7 shows an embodiment of the invention in which a plurality of variable volume containers each containing an amount of fluid are configured into a sheet of columns and rows.

Now referring primarily to FIG. 7, certain embodiments of the invention can provide a plurality of variable volume containers (1) configured as a single integral piece formatted in columns and rows, or otherwise as necessary or desired. A plurality of receptacles (27) configured as a single integral piece formatted in columns and rows can receive the plurality of variable volume containers (1). A releasably sealable closure (20) can be configured to isolate each of the plurality of variable volume containers (1). An amount of gas (6) can be delivered through a gas inlet element (22a) (22b) (two embodiments shown) to the gas collection element (14) within each separate receptacle (27), whether to a single receptacle of the plurality of receptacles or to a plurality of receptacles substantially simultaneously. The amount of gas (6) exerts an amount of pressure (4) on the flexible wall(s) (2) of the individual variable volume containers (1) to generate a fluid stream in one or a plurality of conduits (8) which communicate with each receptacle (27).

Figure 8:
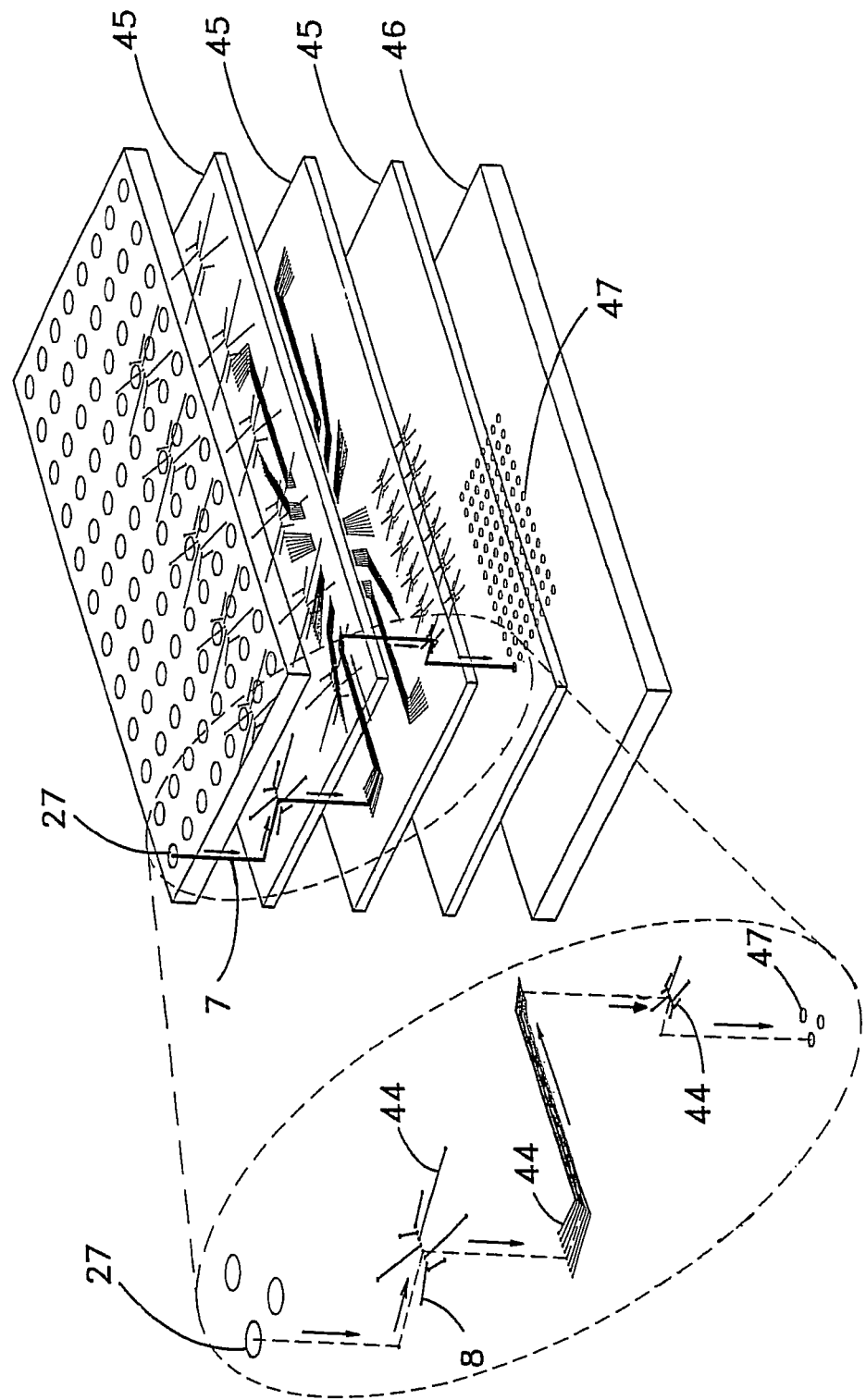
FIG. 8 illustrates a plurality of flow paths operable with the embodiment of the invention shown by FIG. 7.

Now referring primarily to FIG. 8, the conduit (8) which fluidly communicates with each receptacle (27) can comprise a microfluidic conduit (internal diameter of one millimeter or less) such as a plastic tube, or as shown in FIG. 8 can also comprise a relief element (44) in the surface of a single or a plurality of fluid delivery bodies (45) which provides a flow path for the fluid stream (7). The fluid delivery bodies (45) can be releasably sealable and interchangeable to provide a number of different flow paths. In the embodiment shown, the flow path established by the releasably sealable fluid delivery bodies can deliver the fluid (3) from a plurality of variable volume containers (1) to a plate (46) having a plurality of wells (47).

Now referring generally to FIGS. 9-14, the invention further encompasses a numerous and wide variety of compositions. Certain compositions can contain at least an aqueous component, an aqueous miscible alcohol component, and an aqueous-alcohol miscible ketone component. Certain compositions can contain a water miscible solvent combined with water in a proportion substantially able to reduce the number of microorganisms to essentially zero. Since water is strongly hydrogen bonding (two protons per molecule and has a lower dissociation constant than alcohol) as well as strongly polar (higher dipole than ketones), it can be understood that in association with ketones water may exhibit a polar interaction while in association with alcohols water may exhibit a hydrogen bonding interaction.

For example, isopropanol, a secondary alcohol, has two more hydrogen atoms in the molecular structure than the ketone, acetone. One hydrogen can be bound to the 2 position carbon and the second hydrogen can be bound to the oxygen where it can participate in hydrogen bonding. By comparison, acetone does may not have hydrogen atoms that can participate in hydrogen bonding. The C=O bond of acetone provides a dipole with a partial negative charge on the oxygen ("O") that interacts with the partial positive charge of the hydrogen ("H") on the O—H dipole of the water molecule. The relative vapor pressures of isopropanol and acetone (isopropanol 4.1 kPa and acetone 24.7 kPa) provide evidence of the relative strength of the hydrogen bond to that of the polar interaction. Both isopropanol and acetone are each completely miscible with water.

It is also worthwhile to provide the example represented by the pair: 2-butanol (SBA) and 2-butanone (MEK), the four carbon analogs of isopropanol and acetone. While SBA and MEK differ fi-on isopropanol and acetone by only a single carbon ($CH_2$), neither are one hundred percent (100%) miscible with water, having water miscibilities of about twelve and one-half percent (12.5%) and twenty five percent (25%) respectively. However, when combined together in water the total miscibility of the combination can be greater than fifty percent (50%). This synergy can be exploited to increase the amount of certain alcohols or ketones in water. This can be important because the efficacy of these mixtures in killing, disrupting, or solvating living biological particles and non-living components of biological particles can be attributed to the effect of hydrogen bonding, polar interaction, hydrophobic interaction, or amphoteric interactions.

A further advantage of being able to utilize less miscible alcohols and ketones combined with water can be a reduction in the flash point of the mixture. For example, the cyclic six carbon ketone structure of cyclohexanone alone is barely soluble in water (about 2.3 percent), but has a relatively high flash point of 44° C. as compared to −18° C. for acetone. A combination of about ten percent (10%) cyclohexanone, fifty percent (50%) isopropanol, and forty percent (40%) water can be miscible and can have similar or better cleaning, conditioning, disinfection, or decontamination properties compared to using the same mixture of acetone, isopropanol, and water.

The numerous and wide variety of compositions encompassed by the invention generically includes any composition or mixture of between about ten percent (10%) and seventy percent (70%) alcohol by volume and between about two percent (2%) to about thirty five percent (35%) ketone by volume in water. One example of an embodiment of the invention provides a mixture of between forty five percent (45%) and fifty five percent (55%) alcohol, and between about five percent (5%) and about fifteen percent (15%) ketone volume to volume (v/v) in water.

The three components can be combined in various proportions dependent on the application. For example, for the purpose of sterilizing and cleansing the flow path of a microfluidic device utilized to process biological cells such as a flow cytometer and certain applications in liquid chromatography, the amount of alcohol can vary between about fifty percent (50%) and about seventy five percent (75%), while the amount of ketone can vary between about five percent (5%) and about ten percent (10%). By way of contrast, the invention further encompasses embodiments for use in cleaning the flow path of a microfluidic device (16) utilized to process biological macromolecules such as proteins or nucleic acids which may not require sterilization but requires cleaning of deposited hydrophobic material from the surfaces that define the flow path of the microfluidic device. As to these applications preferred compositions in accordance with the invention can include between about twenty five percent (25%) alcohol and about forty percent (45%) alcohol and about fifteen percent (15%) ketone to about thirty five percent (35%) ketone.

With respect to the water utilized in certain embodiments of the invention to clean condition, or disinfect the flow path of microfluidic devices, the water can be an ASTM Type 1-A grade water. This quality may also be preferred for those particular embodiments of the invention contained by the above-described pressure regulated continuously variable volume container. Alternately, with respect to those embodiments of the invention utilized for general cleaning the water quality may be of a lower quality and in some cases only filtered or screened to remove particulate.

A variety of alcohols can be utilized in embodiments of the invention. Methanol, ethanol, isopropanol are typically preferred; however, 1-propanol, 1-butanol, 2-butanol, 1-pentanol, 2-pentanol, isobutanol and various isomers of hexanol can also be utilized in various combinations and permutations.

A variety of ketones can be utilized in embodiments of the invention. Acetone, 2-butanone (MEK), and cyclohexanone are typically preferred; however, 2-pentanone, 3-pentanone, methyl isobutyl ketone, 2-hexanone, 3-hexanone, cyclobutanone, and cyclopentanone can also be utilized in various combinations and permutations.

Individually or in various combinations and permutations, the alcohol and the ketone can be mixed with water to generate a numerous and wide variety of compositions in accordance with the invention. The following list of embodiments of the invention is intended to illustrative rather than limiting with respect to these numerous and varied embodiments:

1. Methanol 50%, Acetone 10%, and water 40% v/v;
2. Methanol 50%, 2-butanone (MEK) 10%, and water 40% v/v;
3. Methanol 50%, Cyclohexanone 10%, and water 40% v/v;
4. Ethanol 50%, Acetone 10%, and water 40% v/v;
5. Ethanol 50%, 2-butanone (MEK) 10%, and water 40% v/v;
6. Ethanol 50%, Cyclohexanone 10%, and water 40% v/v;
7. Isopropanol 50%, Acetone 10%, and water 40% v/v;
8. Isopropanol 50%, 2-butanone (MEK) 10%, and water 40% v/v;
9. Isopropanol 50%, Cyclohexanone 10%, and water 40% v/v;
10. N-propanol 50%, Acetone 10%, and water 40% v/v;
11. N-propanol 50%, 2-butanone (MEK) 10%, and water 40% v/v;
12. N-propanol 50%, Cyclohexanone 10%, and water 40% v/v;
13. 2-butanol (SBA) 50%, Acetone 10%, and water 40% v/v;
14. 2-butanol (SBA) 50%, 2-butanone (MEK) 10%, and water 40% v/v;
15. 2-butanol (SBA) 50%, Cyclohexanone 10%, and water 40% v/v;
16. Methanol 30%, Acetone 30%, and water 40% v/v;
17. Methanol 30%, 2-butanone (MEK) 30%, and water 40% v/v;
18. Methanol 30%, Cyclohexanone 30%, and water 40% v/v;
19. Ethanol 30%, Acetone 30%, and water 40% v/v;
20. Ethanol 30%, 2-butanone (MEK) 30%, and water 40% v/v;
21. Ethanol 30%, Cyclohexanone 30%, and water 40% v/v;
22. Isopropanol 30%, Acetone 30%, and water 40% v/v;
23. Isopropanol 30%, 2-butanone (MEK) 30%, and water 40% v/v;
24. Isopropanol 30%, Cyclohexanone 30%, and water 40% v/v;
25. N-propanol 30%, Acetone 30%, and water 40% v/v;
26. N-propanol 30%, 2-butanone (MEK) 30%, and water 40% v/v;
27. N-propanol 30%, Cyclohexanone 30%, and water 40% v/v;
28. 2-butanol (SBA) 30%, Acetone 30%, and water 40% v/v;
29. 2-butanol (SBA) 30%, 2-butanone (MEK) 30%, and water 40% v/v; or
30. 2-butanol (SBA) 30%, Cyclohexanone 30%, and water 40% v/v.

The invention also encompasses without limitation compositions which include a mixture of water and diacetone alcohol (DAA). Diacetone alcohol (DAA) can be fully miscible in water. In the range of between about ten percent (10%) to about seventy percent (70%) in water, it can be effective as a cleaner, conditioner, or disinfectant in microfluidic devices, such as flow cytometers or liquid chromatographs.

Now referring to FIG. 9, the level of cleaning, conditioning, or disinfecting by embodiments of the invention is illustrated within the flow path of a flow cytometer, or other microfluidic device (16). As shown, the concentration of a first fluid (3) in a microfluidic device, such as a sheath fluid in a flow cytometer, as represented by the solid line (51) comprises one hundred percent of the first fluid (3) in the flow path during normal operation. At the "Start Time" (52) the first fluid (3) is changed so that the second fluid (53) as represented by the hash marked line (54) in FIG. 9 is introduced into the conduit (8) which defines the flow path of the flow cytometer or other microfluidic device (16). At some point in time, the concentration of second fluid (53) will increase to a point called "Action Threshold 1" (55) at which the mixture of the first fluid (3) and the second fluid (53) within the conduit initiates a level of cleaning, conditioning, or disinfecting of the flow path. After elapse of a duration of time, the concentration of the second fluid (53) in the mixture increases to a point called "Action Threshold 2" (56) at which the level of cleaning, conditioning, or disinfecting achieved by the mixture of the first fluid (3) and the second fluid (53) in the flow path is as effective as if only the second fluid (53) were present in the flow path, even though there may still be small amounts of the first fluid (3), such as sheath fluid, present.

A period of "Partial Action" (57) exists between these two points, the duration of which is determined by the volume of the flow path being cleaned, conditioned or disinfected; the rate of flow of the second fluid into the flow path; and by mixing dynamics of the flow path. This period of Partial Action (57) is followed by a period of Full Action (58), which exists for a duration of time until a third fluid (59) is introduced into the flow path of the flow cytometer, or other microfluidic device, to replace, purge or mix with the second fluid in the flow path as represented by the dotted line (60).

In those specific instances in which compositions in accordance with the invention as above-described are used in the flow path of flow cytometers, including, but not limited to, a MoFlo® Flow Cytometer as manufactured by DakoCytomation®, the duration of Partial Action (57) can occur until between about 1.2 to about 1.5 flow path volumes (about 0.4 liters to about 0.5 liters) of the second fluid (53) has been introduced into the flow path of the flow cytometer. The duration of time which elapses in Partial Action (57) can be between about five minutes and about eight minutes when the flow rate at which the second fluid is introduced into the flow path has a rate of between about sixty milliliters (60 mL) per minute and about one hundred milliliters (100 mL) per minute. After the duration of Partial Action (57), the flow rate can reduced to the normal operating conditions of the flow cytometer for ten minutes, which may consume about fifty milliliters (50 mL) of the second fluid. This allows the entire cleaning, conditioning, or disinfecting procedure to be accomplished in a duration of about fifteen minutes with about one-half liter (0.5 L) of any one of the various compositions in accordance with the invention.

Now referring to FIGS. 10A-10C, there can be a variation in fluid dynamics during the change from a first fluid (3) to a second fluid (53) depending on the configuration of the flow path of the flow cytometer or other microfluidic device (16). FIG. 10A represents a microfluidic device (16) in which the flow path volume is relatively small, and in which the flow is not turbulent enough to cause mixing, under this flow condition, embodiments of the invention comprising the second fluid (53) rapidly displace the first fluid (3) volume in the flow path. FIG. 10B represents a microfluidic device (16) in which the flow path has a larger volume or the flow of liquid within the flow path is not entirely laminar. This results in an increase in the amount of time prior to the second fluid (53) displacing the first fluid (3) in the flow path. FIG. 10 C represents a microfluidic device (16) in which the flow path has either a yet greater volume or a yet greater failure in the laminar flow. Again there is an incremental increase in the duration of time to displace the first fluid (3) with the second fluid (53) which can be an embodiment of the invention as above-described.

Now referring to FIG. 11, the conditions within the flow path of a microfluidic device (16) are shown after commencing a rinse step with a third fluid (59) after cleaning, conditioning, or disinfecting the flow path with a second fluid (53) which can be one of the various embodiments of the invention above-described. The concentration of the rinse fluid (59) is shown by the dotted line (60). The rinse fluid (59) can be a reintroduction of the first fluid (3) to the flow path, or another fluid such as water, which acts to displace the second fluid (53). At some point in time, the "Return Threshold" (61) will be reached at which time the cleaning, conditioning, or disinfecting composition in accordance with invention has not fully been displaced, but it is at a level which no longer can effect the performance of the microfluidic device (16).

In the case of conventional cleaning compositions such as sodium chlorite, the Return Threshold (61) may have three attributes to consider, namely the oxidative power of the remaining chlorine dioxide gas or chlorine gas to damage the biological particles being analyzed, the foaming characteristics of remaining detergent, and the evolution of gas bubbles.

In the case of utilizing embodiments of the invention, the Return Threshold (61) can primarily be related to the maximum tolerable concentrations of alcohol and ketone by the biological particles (33) being analyzed. Since low molecular weight C2, C3, and C4 alcohols are non-reactive and are typically not toxic at levels below one percent (1%), and since ketones such as acetone can be naturally occurring in metabolism, a one hundred fold (100 fold) dilution of a cleaning, conditioning, or disinfecting composition in accordance with the invention (such as 50% isopropanol and 10% acetone in water 40% v/v or such as 40% diacetone alcohol (DAA) in water 60% v/v) can be adequate to achieve the Return Threshold (61).

Now referring primarily to FIG. 12, which provides a non-limiting exemplary application utilizing the invention, the cleaning, conditioning, or disinfection procedure can have three steps with respect to a flow cytometer:

1. A first Period A (62) of about five minutes to displace the first fluid (sheath fluid) in the flow path of the flow cytometer with a second fluid (53) being an embodiment of the invention;
2. A second Period B (63) of about ten minutes (10 minutes) to clean, condition or disinfect the flow path of the flow cytometer with an embodiment of the invention in accordance with the description above; and
3. A third Period C (64) of about fifteen minutes (15 minutes) to displace the second fluid (53) with sheath fluid (3) and re-equilibrate the flow path to the operating condition.

A preferred embodiment of this three step process can utilize as a second fluid (53) of 50% isopropanol—10% acetone v/v in water. Another preferred embodiment of this 3 step process can utilize a second fluid (53) of 40% diacetone alcohol (DAA) v/v in water. An additional step can provide for introducing water or other third fluid (59) into the flow path of the flow cytometer prior to the step of re-introducing sheath fluid (3) to displace the second fluid (53).

TABLE 1

|  |  | Alcohol Conc. | Ketone Conc. |
|---|---|---|---|
| 1A | | | |
| ONE HALF | 0.5 | 50.00% | 10.00% |
| 1 | 0.5 | 25.0000% | 5.0000% |
| 2 | 0.25 | 12.5000% | 2.5000% |
| 3 | 0.125 | 6.2500% | 1.2500% |
| 4 | 0.0625 | 3.1250% | 0.6250% |
| 5 | 0.03125 | 1.5625% | 0.3125% |
| 6 | 0.015625 | 0.7813% | 0.1563% |
| 7 | 0.007813 | 0.3906% | 0.0781% |
| 8 | 0.003906 | 0.1953% | 0.0391% |
| 9 | 0.001953 | 0.0977% | 0.0195% |
| 10 | 0.000977 | 0.0488% | 0.0098% |
| 11 | 0.000488 | 0.0244% | 0.0049% |
| 12 | 0.000244 | 0.0122% | 0.0024% |
| 1B | | | |
| ONE THIRD | 0.33 | 50.00% | 10.00% |
| 1 | 0.33 | 16.5000% | 3.3000% |
| 2 | 0.1089 | 5.4450% | 1.0890% |
| 3 | 0.035937 | 1.7969% | 0.3594% |
| 4 | 0.011859 | 0.5930% | 0.1186% |
| 5 | 0.003914 | 0.1957% | 0.0391% |
| 6 | 0.001291 | 0.0646% | 0.0129% |
| 7 | 0.000426 | 0.0213% | 0.0043% |
| 8 | 0.000141 | 0.0070% | 0.0014% |
| 9 | 4.64E−05 | 0.0023% | 0.0005% |
| 10 | 1.53E−05 | 0.0008% | 0.0002% |
| 11 | 5.05E−06 | 0.0003% | 0.0001% |
| 12 | 1.67E−06 | 0.0001% | 0.0000% |

TABLE 1-continued

|  |  | Alcohol Conc. | Ketone Conc. |
|---|---|---|---|
|  |  | 1C |  |
| ONE FOURTH |  | 0.25 | 50.00% | 10.00% |
|  | 1 | 0.25 | 12.5000% | 2.5000% |
|  | 2 | 0.0625 | 3.1250% | 0.6250% |
|  | 3 | 0.015625 | 0.7813% | 0.1563% |
|  | 4 | 0.003906 | 0.1953% | 0.0391% |
|  | 5 | 0.000977 | 0.0488% | 0.0098% |
|  | 6 | 0.000244 | 0.0122% | 0.0024% |
|  | 7 | 6.1E−05 | 0.0031% | 0.0006% |
|  | 8 | 1.53E−05 | 0.0008% | 0.0002% |
|  | 9 | 3.81E−06 | 0.0002% | 0.0000% |
|  | 10 | 9.54E−07 | 0.0000% | 0.0000% |
|  | 11 | 2.38E−07 | 0.0000% | 0.0000% |
|  | 12 | 5.96E−08 | 0.0000% | 0.0000% |

Now referring to Table 1, a mathematical model is provided useful in understanding the displacement of a first fluid (3) with a second fluid (which can be a composition in accordance with the invention) (53) in the flow path of an exemplary microfluidic device.

As one example of compositions in accordance with the invention, an aqueous mixture of 50% alcohol, 10% ketone and 40% water, comprise a first fluid (3), namely a cleaning fluid. As a volume of a second fluid (53), in this example water, flows into the fluidic supply of a microfluidic device, the second fluid (53) will dilute the first fluid (3) progressively. In this example, one would consider this to describe the rinsing out of a cleaning solution by a water wash. It could also, in other examples, describe the addition of a cleaning solution to effect cleaning, or the addition of a working solution, such as sheath fluid or a phosphate buffered saline solution, or the like, which is used to analyze or sort particles or cells.

In this example, a parameter of the operating procedure might be that the second fluid (53) should flow into the microfluidic device until a point when the concentration of alcohol is less than 1% and the concentration of the ketone is less than 0.2%. This may be considered to be the Return Threshold (61). Since the total volume of the fluidic device is known, and the flow rate of the second fluid (53) into the fluidic device is also known, the amount of fluid needed to fully replace the first fluid (3), namely, cleaning, disinfection and conditioning fluid, with the second fluid (53), namely water, can be modeled as the number of full volume exchanges of the fluidic system.

Although fluidic systems can be complicated, with different compartments which may have different volumes and different mixing properties, it can be the case that a certain large volume, such as a particle filter housing, may be the dominant volume in the system and the volume and mixing properties of fluid in that housing may most limit. Table 1, and respectively tables 1A, 1B, and 1C, show the expected concentrations of alcohol and ketone which are present after each of 12 exchanges of volume, where dilutions occur at 2×, 3× and 4× respectively.

It can be seen in table 1A, that a 2× dilution rate, resulting in a final concentration of 1/2 per volume change, will establish the correct above mentioned operating condition (1% alcohol, 0.2% ketone) after 6 volume changes.

It can be seen in table 1B, that a 3× dilution rate, resulting in a final concentration of 1/3 per volume change, will establish the correct above mentioned operating condition (1% alcohol, 0.2% ketone) after 4 volume changes.

It can be seen in table 1C, that a 4× dilution rate, resulting in a final concentration of 1/4 per volume change, will establish the correct above mentioned operating condition (1% alcohol, 0.2% ketone) after 3 volume changes.

Importantly, this model shows that for various fluidic devices which may have different configurations of fluid volumes and fluid flow, and for various solutions made in accordance with the invention, such as cleaning solutions, which may require different amounts of time to clean, decontaminate and condition the fluidic system, and which may have different low concentrations which define a Return Threshold, an ideal operating procedure may be designed and tested, which minimizes, for example, the time spent in cleaning, or maximizes, as other example, the extent of cleaning.

This mathematical model was used to determine, with minimal experimentation, an effective cleaning procedure using the instant invention for the cleaning, disinfection and conditioning of the fluidic portions of a MoFlo® flow cytometer. For an embodiment of this invention which is able to effect cleaning, disinfection and conditioning by a 5 minute interval of fully concentrated cleaning solution, a procedure was derived which allowed the following procedure:

From a condition representing an operating MoFlo® flow cytometer which is currently sorting particles, namely sperm particles, and is scheduled for a cleaning procedure, a cleaning solution in accordance with this invention flows into the flow cytometer for a period of 15 minutes. Then, a water solution is used to rinse the flow cytometer for 5 minutes. Then a sheath fluid is used to rinse the flow cytometer for 10 minutes. Then the instrument is returned to standard operation of sorting sperm.

Now referring primarily to FIG. 13, the results of a test are shown in which *E. coli* ATCC 9027 grown overnight in nutrient agar is challenged with the conventional cleaning compositions Alcide Corporation EXSPOR® (65), bleach (66), and a second conventional flow cytometer cleaning solution (68) (product "A"); a particular embodiment of the invention comprising isopropanol fifty percent volume to volume (50% v/v) and acetone ten percent volume to volume (10% v/v) in water (67); and a Peptone control (69), each ninety nine parts (99 parts) of the cleaning composition or of the inventive composition isopropanol fifty percent volume to volume (50% v/v) and acetone ten percent volume to volume (10% v/v) in water (67) to one part (1 part) *E. Coli* suspension for a duration of either five minutes, ten minutes, fifteen minutes, thirty minutes, or forty five minutes.

Referring specifically to FIG. 13, the graph and Table 2 (colony forming units under the rows) show EXSPOR® (65), bleach (66), the particular embodiment of the invention comprising isopropanol fifty percent volume to volume (50% v/v) and acetone ten percent volume to volume (10% v/v) in water (67) (designated as IPA:ACE in FIG. 13) were effective in generating a one hundred percent (100%) kill rate (100% reduction in number of microorganisms) within five minutes, while product "A" the conventional flow cytometer cleaning solution (68) and the control were less effective. The example is not intended to limit the invention to this particular composition, this particular organism, or to this particular duration of time, but rather to be illustrative with respect to the numerous and wide variety of embodiments of the invention which can be used to kill the wide variety of organisms which can populate the flow paths of microfluidic devices.

Now referring to FIG. 14, the results of a test are shown in which *P. aeruginosa* MRI Ps 10 grown overnight in nutrient agar is challenged with the conventional cleaning compositions EXSPOR® (65), bleach (66), and product "A" (68); a particular embodiment of the invention comprising isopropanol fifty percent volume to volume (50% v/v) and acetone ten percent volume to volume (10% v/v) in water (67) (designated as IPA:ACE in FIG. 14); and a Peptone control (69), each ninety nine parts (99 parts) of the cleaning composition or of the composition in accordance with the invention to one part (1 part) *E. Coli* suspension for a duration of either five minutes, ten minutes, fifteen minutes, thirty minutes, or forty five minutes.

Referring specifically to FIG. 14, the graph and Table 3 (colony forming units under the rows) show EXSPOR® (65), bleach (66), and the particular embodiment of the invention comprising isopropanol fifty percent volume to volume (50% v/v) and acetone ten percent volume to volume (10% v/v) in water (67) (IPA:ACE) were effective in generating a one hundred percent (100%) kill rate within five minutes, while the conventional product "A" flow cytometer cleaning solution (68) and the control were less effective. The example is not intended to limit the invention to this particular composition, this particular organism, or to this particular duration of time, but rather to be illustrative with respect to the numerous and wide variety of embodiments of the invention which can be used to kill the wide variety of organisms which can populate the flow paths of microfluidic devices.

V. EXAMPLES

Example 1

Now referring to FIG. 8, which shows a bivariate plot generated from the analysis of fluorochrome stained sperm cells differentiated based upon the presence of an X-chromosome or a Y-chromosome utilizing a DakoCytomation, Inc., MoFlo® flow cytometer in accordance with the invention. A conventional sheath fluid tank was retrofitted with a variable volume container in accordance with the invention containing about 4 liters of sterile sheath fluid. The sheath fluid was maintained at about 20° C. during use. An amount of gas was delivered to the sealed sheath fluid tank to exert an amount of gas pressure on the exterior surface of the variable volume container resulting in the generation of a fluid stream within the flow path of a DakoCytomation, Inc., MoFlo® flow cytometer. The flow cytometer was then otherwise operated in accordance with the standard operation procedures provided by DakoCytomation, Inc. for a period of about 8 hours to analyze and sort a mixture of sperm cells to generate a viable population of X-chromosome bearing spermatozoa and viable population of Y-chromosome bearing spermatozoa. X-chromosome bearing and Y-chromosome bearing populations enriched were established in discrete collection containers.

Example 2

Similarly, a flow cytometer sorting human sperm in accordance with the invention can provide X-chromosome bearing and Y-chromosome bearing populations for the purpose of sex selected artificial insemination. Human sperm cells sufficient for artificial insemination of a human female can be flow sorted in approximately 2 hours from male human ejaculate. The enriched X-chromosome bearing or Y-chromosome bearing sperm cell populations are typically over 80% pure. Clinical procedures may require that after each sample is sorted, the sorting fluidic channels are washed with an acid wash, a base wash, a disinfectant wash, and then a water wash. The instant invention can be used to deliver four different sterile fluids to the flow cytometer, and allows computer automated cleaning steps to be performed between patients. During the automated wash procedure, the physician may perform the artificial insemination procedure.

Example 3

In accordance with the invention, a plurality of different microfluidic devices can be operating 24 hours per day. The variable volume containers can be located in common receptacle pressured at about 1.6 atmospheres. Each microfluidic device can be served with one or more conduits from the variable volume containers which communicate with the conventional hardware of the microfluidic device.

Example 4

Freshly cultivated cultures of *E. coli* (ATCC 25922, MRI EC 13) and *Pseudomonas aeruginosa* (ATCC 9027, MRI Ps 10) were suspended in MHB (Mueller-Hinton Broth) nutrient broth at $10^8$ cfu/ml (colony-forming units per milliliter), diluted about 1:10 in peptone nutrient broth to about $10^7$ cfu/ml. About 1 ml of each of the diluted cultures was added to one each of 9 ml of the corresponding test solutions described below for 5.0 minutes and then diluted in two steps of 1:10 per step. 100 microliters of such diluted culture was then plated onto a conventional nutrient agar plate. Nutrient agar plates were incubated by conventional methods and the number of colonies present on each plate were counted. Positive controls combined freshly cultivated cultures above described with peptone broth were included in each test group and numbers of colonies in control plates were used as a reference.

The following compositions were used as test solutions:
1. Isopropanol (IPA) 50%, Acetone (ACE) 10%, and water 40% v/v;
2. Isopropanol (IPA) 40%, Acetone (ACE) 8%, and water 52% v/v;
3. Isopropanol (IPA) 30%, Acetone (ACE) 6%, and water 64% v/v;
4. Isopropanol (IPA) 20%, Acetone (ACE) 4%, and water 76% v/v;
5. Isopropanol (IPA) 16.5%, Acetone (ACE) 3.3%, and water 80.2% v/v;
6. Isopropanol (IPA) 12.5%, Acetone (ACE) 2.5%, and water 85% v/v;
7. Isopropanol (IPA) 10%, Acetone (ACE) 2%, and water 88% v/v;
8. Isopropanol (IPA) 8.33%, Acetone (ACE) 1.66%, and water 90% v/v;
9. Isopropanol (IPA) 5%, Acetone (ACE) 1%, and water 94% v/v;
10. Isopropanol (IPA) 2.5%, Acetone (ACE) 0.50%, and water 97% v/v;
11. Isopropanol (IPA) 5%, Acetone (ACE) 50%, and water 90% v/v;
12. Isopropanol (IPA) 7.5%, Acetone (ACE) 7.5%, and water 85% v/v;
13. Isopropanol (IPA) 10%, Acetone (ACE) 10%, and water 80% v/v;
14. Diacetone Alcohol (DAA) 60%, and water 40% v/v;
15. Diacetone Alcohol (DAA) 48%, and water 52% v/v;
16. Diacetone Alcohol (DAA) 36%, and water 64% v/v;
17. Diacetone Alcohol (DAA) 24%, and water 76% v/v;
18. Diacetone Alcohol (DAA) 20%, and water 80% v/v;
19. Diacetone Alcohol (DAA) 15%, and water 85% v/v;
20. Diacetone Alcohol (DAA) 12%, and water 88% v/v;
21. Diacetone Alcohol (DAA) 10%, and water 90% v/v;
22. Diacetone Alcohol (DAA) 6%, and water 94% v/v;

23. Diacetone Alcohol (DAA) 3%, and water 97% v/v;
24. Methanol (MeOH) 10%, and water 90% v/v;
25. Methanol (MeOH) 15%, and water 85% v/v;
26. Methanol (MeOH) 20%, and water 80% v/v;
27. Ethanol (EtOH) 10%, and water 90% v/v;
28. Ethanol (EtOH) 15%, and water 85% v/v;
29. Ethanol (EtOH) 20%, and water 80% v/v;
30. Isopropanol (IPA) 10%, and water 90% v/v;
31. Isopropanol (IPA) 15%, and water 85% v/v;
32. Isopropanol (IPA) 20%, and water 80% v/v;
33. 2-Butanol (SBA) 10%, and water 90% v/v;
34. 2-Butanol (SBA) 15%, and water 85% v/v;
35. 2-Butanol (SBA) 20%, and water 80% v/v;
36. Acetone (ACE) 10%, and water 90% v/v;
37. Acetone (ACE) 15%, and water 85% v/v;
38. Acetone (ACE) 20%, and water 80% v/v;
39. 2-butanone (MEK) 10%, and water 90% v/v;
40. 2-butanone (MEK) 15%, and water 85% v/v;
41. 2-butanone (MEK) 20%, and water 80% v/v;
42. 2-Butanol (SBA) 8.3%, 2-butanone (MEK) 1.7%, and water 90% v/v
43. 2-Butanol (SBA) 12.5%, 2-butanone (MEK) 2.5%, and water 85% v/v
44. 2-Butanol (SBA) 16.5%, 2-butanone (MEK) 3.3%, and water 80% v/v
45. 2-Butanol (SBA) 5%, 2-butanone (MEK) 5%, and water 90% v/v
46. 2-Butanol (SBA) 7.5%, 2-butanone (MEK) 7.5%, and water 85% v/v
47. 2-Butanol (SBA) 10%, 2-butanone (MEK) 10%, and water 80% v/v
48. Isopropanol (IPA) 50%, 2-butanone (MEK) 10%, and water 40% v/v
49. Isopropanol (IPA) 30%, 2-butanone (MEK) 30%, and water 40% v/v
50. Isopropanol (IPA) 30%, 2-butanone (MEK) 6%, and water 64% v/v
51. Isopropanol (IPA) 10%, 2-butanone (MEK) 2%, and water 88% v/v
52. Isopropanol (IPA) 8.3%, Cyclohexanone (CYH=0) 1.7%, and water 90% v/v
53. Isopropanol (IPA) 12.5%, Cyclohexanone (CYH=0) 2.5%, and water 85% v/v
54. Isopropanol (IPA) 16.5%, Cyclohexanone (CYH=0) 3.5%, and water 80% v/v
55. 2-butanone oxime (30%) and water (70%) v/v
56. 2-butoxyethanol (30%) and water (70%) v/v
57. 2-ethoxyethanol (30%) and water (70%) v/v
58. 2-ethoxyethylacetate (30%) and water (70%) v/v
59. 5-hydroxy-4-octanone (30%) and water (70%) v/v
60. 2-methyl-2,4-pentandiol (30%) and water (70%) v/v
61. 1,2-ethandiol, diacetate (30%) and water (70%) v/v
62. 2,5-hexanedione (30%) and water (70%) v/v Now referring to Table 4, the results of combining each test solution as described above with each of the E. coli (ATCC 25922, MRI EC 13) and Pseudomonas aeruginosa (ATCC 9027, MRI Ps 10) cultures are summarized using the following quantitative nomenclature:
1) "XXX" denotes a plate in which zero colonies were present, representing complete reduction of the number of microorganisms.
2) "XXx" denotes a plate where only one colony was present, representing nearly complete reduction of the number of microorganisms.
3) "XX" denotes a plate where the numbers of colonies represented less than 10% of the number of colonies counted in the corresponding positive control plate, representing a significant reduction of the number of microorganisms.
4) "X" denotes a plate where the numbers of colonies represented less than 50% of the number of colonies counted in the corresponding positive control plate, representing reduction of the number of microorganisms.
5) "- - - 0 - - -" denotes a plate where the numbers of colonies represented more than 50% of the number of colonies counted in the corresponding positive control plate, representing no significant reduction of the number of microorganisms.

As can be understood from the summary of results of the 62 test samples, the combination of diacetone alcohol (DAA) (between about 10% and 60% v/v) with water was effective in reducing the number of colonies counted or viable microorganisms in the test sample to zero. The mixtures of diacetone alcohol (DAA) tested all have a higher flash point and lower vapor pressure than isopropanol and all aqueous mixtures of diacetone alcohol (DAA) also confer the benefits above described of being categorized as "combustible" rather than "flammable" for the purpose of transporting the mixtures worldwide.

Similarly, 2-butanone oxime (30%) and water (70%) v/v; 2-butoxyethanol (30%) and water (70%) v/v; 2-ethoxyethylacetate (30%) and water (70%) v/v; 5-hydroxy-4-octanone (30%) and water (70%) v/v; 1,2-ethandiol, diacetate (30%) and water (70%) v/v; 2,5-hexanedione (30%) and water (70%) v/v were each effective in reducing the number of colonies counted or viable microorganisms in the test sample to zero. Each may have a higher flash point and lower vapor pressure than isopropyl alcohol and these aqueous mixtures of DAA may also confer the benefits above described of being categorized as "combustible" rather than "flammable" or may be less flammable than isopropanol for the purpose of transporting the mixtures worldwide.

The various combinations of isopropanol, cyclohexanone, and water and the various combinations of 2-butanol (SBA), 2-butanone (MEK), and water shown by the table appear to be more effective in reducing the number of viable microorganisms than a similar volume of isopropanol and water alone and such combinations may also provide the benefits of a higher flash point, lower vapor pressure, and lower flammability than isopropanol in water.

Certain combinations of isopropanol and acetone and isopropanol and 2-butanone (MEK) also appear to be effective in reducing the number of viable microorganisms in test samples to zero.

Interestingly, each of methanol and ethanol which are commonly utilized to clean and disinfect microfluidic devices such as flow cytometers do not appear to be effective in aqueous mixtures of up to 20% v/v or may not be as effective as any of diacetone alcohol (DAA), isopropanol, 2-butanol (SBA), 2-butanone (MEK) utilized separately and such effective compositions of the instant invention do not appear to have been utilized for the cleaning, conditioning, or disinfection of microfluid devices, and specifically not flow cytometers.

TABLE 4

| component 1 | % v/v | component 2 | % v/v | TEST EC 13 | TEST Ps 10 |
|---|---|---|---|---|---|
| IPA | 50% | ACE | 10% | XXX | XXX |
| IPA | 40% | ACE | 8% | XXX | XXX |
| IPA | 30% | ACE | 6% | XXX | XXX |
| IPA | 20% | ACE | 4% | XXx | XXX |

TABLE 4-continued

| component 1 | % v/v | component 2 | % v/v | TEST EC 13 | TEST Ps 10 |
|---|---|---|---|---|---|
| IPA | 16.5% | ACE | 3.3% | XXX | XXX |
| IPA | 12.5% | ACE | 2.5% | XX | XXX |
| IPA | 10% | ACE | 2% | ---o--- | ---o--- |
| IPA | 8.3% | ACE | 1.66% | ---o--- | ---o--- |
| IPA | 5% | ACE | 1% | ---o--- | ---o--- |
| IPA | 2.5% | ACE | 0.50% | ---o--- | ---o--- |
| IPA | 5% | ACE | 5% | ---o--- | ---o--- |
| IPA | 7.5% | ACE | 7.5% | ---o--- | XXx |
| IPA | 10.0% | ACE | 10.0% | XXX | XXX |
| DAA | 60% | | | XXX | XXX |
| DAA | 48% | | | XXX | XXX |
| DAA | 36% | | | XXX | XXX |
| DAA | 24% | | | XXX | XXX |
| DAA | 20% | | | XXX | XXX |
| DAA | 15% | | | XXX | XXX |
| DAA | 12% | | | XXX | XXX |
| DAA | 10% | | | XXX | XXX |
| DAA | 6% | | | X | X |
| DAA | 3% | | | ---o--- | ---o--- |
| MeOH | 10% | | | ---o--- | ---o--- |
| MeOH | 15% | | | ---o--- | ---o--- |
| MeOH | 20% | | | ---o--- | ---o--- |
| EtOH | 10% | | | ---o--- | ---o--- |
| EtOH | 15% | | | ---o--- | ---o--- |
| EtOH | 20% | | | ---o--- | XXX |
| IPA | 10% | | | X | XXX |
| IPA | 15% | | | XXX | XXX |
| IPA | 20% | | | XXX | XXX |
| SBA | 10% | | | XXX | XXX |
| SBA | 15% | | | XXX | XXX |
| SBA | 20% | | | XXX | XXX |
| ACE | 10% | | | ---o--- | ---o--- |
| ACE | 15% | | | X | X |
| ACE | 20% | | | XX | XXx |
| MEK | 10% | | | XXX | XXX |
| MEK | 15% | | | XXX | XXx |
| MEK | 20% | | | XXX | XXX |
| SBA | 8.3% | MEK | 1.7% | XXX | XXX |
| SBA | 12.5% | MEK | 2.5% | XXX | XXX |
| SBA | 16.5% | MEK | 3.3% | XXX | XXX |
| SBA | 5% | MEK | 5% | XXX | XXX |
| SBA | 7.5% | MEK | 7.5% | XXX | XXX |
| SBA | 10% | MEK | 10% | XXX | XXX |
| IPA | 50% | MEK | 10% | XXX | XXX |
| IPA | 30% | MEK | 30% | XXX | XXX |
| IPA | 30% | MEK | 6% | XXX | XXX |
| IPA | 10% | MEK | 2% | ---o--- | ---o--- |
| IPA | 8.3% | CyH=O | 1.7% | XXX | XXX |
| IPA | 12.5% | CyH=O | 2.5% | XXX | XXX |
| IPA | 16.5% | CyH=O | 3.3% | XXX | XXX |
| 2-butanone oxime | 30% | | | XXX | XXX |
| 2-butoxy ethanol | 30% | | | XXX | XXX |
| 2-ethoxy ethanol | 30% | | | ---o--- | ---o--- |
| 2-ethoxy ethylacetate | 30% | | | XXX | XXX |
| 5-hydroxy-4-octanone | 30% | | | XXX | XXX |
| 2-methyl-2,4 pentandiol | 30% | | | X | XXx |
| 1,2-ethandiol, diacetate | 30% | | | XXX | XXX |
| 2,5 hexanedione | 30% | | | XXX | XXX |

Example 5

Freshly cultivated cultures of *E. coli* (ATCC 25922, MRI EC 13) and *Pseudomonas aeruginosa* (ATCC 9027, MRI Ps 10) were suspended in MHB nutrient broth at $10^8$ cfu/ml (colony forming units per milliliter), diluted about 1:10 in peptone nutrient broth to about $10^7$ cfu/ml. About 1 ml of each of the diluted cultures was added to one each of 9 ml of the corresponding test solutions described below for 30 seconds and then diluted in two steps of 1:10 per step. 100 microliters of such diluted culture was then plated onto a conventional nutrient agar plate. Nutrient agar plates were incubated by conventional methods and the number of colonies present on each plate were counted. Positive controls combined freshly cultivated cultures above described with peptone broth were included in each test group and numbers of colonies in control plates were used as a reference.

The following compositions were used as test solutions:
55. 2-butanone oxime (30%) and water (70%) v/v
56. 2-butoxyethanol (30%) and water (70%) v/v
57. 2-ethoxyethanol (30%) and water (70%) v/v
58. 2-ethoxyethylacetate (30%) and water (70%) v/v
59. 5-hydroxy-4-octanone (30%) and water (70%) v/v
60. 2-methyl-2,4-pentandiol (30%) and water (70%) v/v
61. 1,2-ethandiol, diacetate (30%) and water (70%) v/v
62. 2,5-hexanedione (30%) and water (70%) v/v Now referring to Table 5, the results of combining each test solution as described above with each of the *E. coli* (ATCC 25922, MRI EC 13) and *Pseudomonas aeruginosa* (ATCC 9027, MRI Ps 10) cultures are summarized using the following quantitative nomenclature:

1) "XXX" denotes a plate in which zero colonies were present, representing complete reduction of the number of microorganisms.

2) "XXx" denotes a plate where only one colony was present, representing nearly complete reduction of the number of microorganisms.

3) "XX" denotes a plate where the numbers of colonies represented less than 10% of the number of colonies counted in the corresponding positive control plate, representing a significant reduction of the number of microorganisms.

4) "X" denotes a plate where the numbers of colonies represented less than 50% of the number of colonies counted in the corresponding positive control plate, representing reduction of the number of microorganisms.

5) "- - - 0 - - -" denotes a plate where the numbers of colonies represented more than 50% of the number of colonies counted in the corresponding positive control plate, representing no significant reduction of the number of microorganisms.

TABLE 5

| component 1 | % v/v | component 2 | % v/v | TEST EC 13 | TEST Ps 10 |
|---|---|---|---|---|---|
| 2-butanone oxime | 30% | | | XXX | XXX |
| 2-butoxy ethanol | 30% | | | XXX | XXX |
| 2-ethoxy ethanol | 30% | | | ---o--- | ---o--- |
| 2-ethoxy ethylacetate | 30% | | | XXX | XXX |
| 5-hydroxy-4-octanone | 30% | | | XXX | XXX |
| 2-methyl-2,4 pentandiol | 30% | | | X | ---o--- |
| 1,2-ethandiol, diacetate | 30% | | | XXX | XXX |
| 2,5 hexanedione | 30% | | | XXX | XXX |

Example 6

Compositions conventionally utilized to reduce the number of microorganisms in microfluidic devices such as 70% isopropanol, 70% ethanol or 15% bleach solution were compared to certain inventive compositions utilized to reduce the number of microorganisms in microfluidic devices, such as 50% isopropanol, 10% acetone in water v/v, and 36% diacetone alcohol (DAA) in water v/v.

Freshly cultivated cultures of *Staphylococcus aureus* (ATCC 6538, MRI Sta 21), *Bacillus subtilis* (ATCC 6633, MRI BS 1), *Pseudomonas aeruginosa* (ATCC 9027, MRI Ps 10), *Candida albicans* (ATCC 10231, MRI CA 2), *Aspergillus niger* (ATCC 16404, MRI AN 2), and *Clostridium sporogenes* (ATCC 19404, MRI Cl 12) were suspended in MHB nutrient broth at $10^8$ cfu/ml (colony forming units per milliliter), diluted 1:10 in peptone nutrient broth to $10^7$ cfu/ml. About 1 ml of each of the diluted cultures was added to one each of 9 ml of the corresponding test solutions described below for 5.0 minutes and then diluted in two steps of 1:10 per step. 100 microliters of such diluted culture was then plated onto a conventional nutrient agar plate. Nutrient agar plates were incubated by conventional methods and the number of colonies present on each plate were counted. Positive controls combined freshly cultivated cultures above described with peptone broth were included in each test group and numbers of colonies in control plates were used as a reference.

The following compositions were used as test solutions:
1. Isopropanol (IPA) 50%, Acetone (ACE) 10%, and water 40% v/v;
2. Diacetone Alcohol (DAA) 36% and water 64% v/v;
3. Ethanol (EtOH) 70% and water 30% v/v;
4. Isopropanol (IPA) 70% and water 30% v/v;
5. Bleach 15%, and water 85 v/v.

Now referring to Table 6, the results of combining each test solution as described above with each of the *Staphylococcus aureus* (ATCC 6538, MRI Sta 21), *Bacillus subtilis* (ATCC 6633, MRI BS 1), *Pseudomonas aeruginosa* (ATCC 9027, MRI Ps 10), *Candida albicans* (ATCC 10231, MRI CA 2), *Aspergillus niger* (ATCC 16404, MRI AN 2), and *Clostridium sporogenes* (ATCC 19404, MRI Cl 12) cultures are summarized using the following quantitative nomenclature:
1) "XXX" denotes a plate in which zero colonies were present, representing complete reduction of the number of microorganisms.
2) "XXx" denotes a plate where only one colony was present, representing nearly complete reduction of the number of microorganisms.
3) "XX" denotes a plate where the numbers of colonies represented less than 10% of the number of colonies counted in the corresponding positive control plate, representing a significant reduction of the number of microorganisms.
4) "X" denotes a plate where the numbers of colonies represented less than 50% of the number of colonies counted in the corresponding positive control plate, representing reduction of the number of microorganisms.
5) "- - - 0 - - -" denotes a plate where the numbers of colonies represented more than 50% of the number of colonies counted in the corresponding positive control plate, representing no significant reduction of the number of microorganisms.

TABLE 6

| | | | | Sta 21 | BS 1 | Ps 10 | CA 2 | AN 2 | Cl 12 |
|---|---|---|---|---|---|---|---|---|---|
| IPA | 50% | ACE | 10% | XXX | XXX | XXX | XXX | XXX | XXX |
| DAA | 36% | | | XXX | XXX | XXX | XXX | XXX | XXx |
| EtOH | 70% | | | XXX | XXX | XXX | XXX | XXX | XXX |
| IPA | 70% | | | XX | XXX | XXX | XXX | XXX | XXx |
| Bleach | 15% | | | XXX | XXX | XXX | XXX | XXX | XXX |

As can be understood from the summary of results of the five test samples in Table 6, the combination of about 50% isopropanol, about 10% acetone, and about 40% water v/v; and the combination of about 36% diacetone alcohol (DAA) in about 64% water were each as effective or nearly as effective as each of 15% bleach, 70% ethanol, or 70% isopropanol each combined with water v/v. As above-described, diacetone alcohol (DAA) and combinations of isopropanol with a ketone can confer advantages beyond reducing the number of microorganisms in a microfluidic device to zero, including being categorized for transportation as a "combustible" or being less flammable composition, or having a lower vapor pressure, or a higher flash point.

Also, based on the various tests performed, the following compositions when combined with water will likely be effective in reducing the number of microorganisms in the flow path of a microfluidic device: 2-butoxymethanol, 2-butoxyethanol, 2-butanone oxime, 2-methyl-2,4 pentandiol 2-methoxymethanol, 2-ethoxyethanol, 2-ethoxyethylacetate, 2-butoxyethylacetate, 2-methoxyethylacetate, 1,2-ethandiol diacetate, 2,6-dimethylpyridine, 4-methylpyridine, pyridine, 4-methyl-4-penten-2-ol, 4-methyl-4-penten-2-one, 2,3'-hexanedione, 2,4-hexanedione, 2,5-hexanedione, 5-hydroxy-4-octanone, hydroxyacetone, 3-pentanone.

As can be easily understood from the foregoing, the basic concepts of the present invention may be embodied in a variety of ways. The invention involves numerous and varied embodiments of a continuously variable volume container for fluid delivery and methods of making and using such continuously variable volume container.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "adjustable volume" should be understood to encompass disclosure of the act of "adjusting volume"—whether explicitly discussed or not—and, conversely, were there effectively disclosure of the act of "adjusting volume", such a disclosure should be understood to encompass disclosure of an "adjustable volume" and even a "means for adjusting volume." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

We claim:
1. A method of reducing a number of viable microorganisms in a flow path of a microfluidic device, comprising:
   a) flowing an amount of an antimicrobial composition within said flow path, wherein said antimicrobial composition includes:
      i. an antimicrobially active agent of an alcohol between about 10% and about 55% by volume selected from the group consisting of methanol, ethanol, N-propanol, isopropanol, 2-butanol, n-butanol and isobutanol, and a ketone between about 2% and about 35% by volume selected from the group consisting of acetone, 2-butanone, cyclohexanone, 2-pentanone, 3-pentanone, 2-hexanone, 3-hexanone, methyl isobutyl ketone, cyclobutanone, and cyclopentanone, said alcohol and said ketone being the only effective antimicrobially active components in said antimicrobial composition; and ii. an inactive agent comprising water, wherein said alcohol and said ketone remain miscible in said water; and b) contacting said viable microorganisms in said flow path of said microfluidic device with said antimicrobial composition; and c) killing viable microorganisms in said flow path by greater than a 2-$\log_{10}$ order within a time period of fifteen minutes of contacting said viable microorganisms with said antimicrobial composition.

2. The method of reducing a number of viable microorganisms in the flow path of claim 1, wherein said amount of alcohol is between about 30% and about 50% by volume, and wherein said amount of ketone is between about 10% and about 30% by volume.

3. The method of reducing a number of viable microorganisms in the flow path of claim 1, wherein said antimicrobial composition is selected from the group consisting of:

a) methanol about 50%, acetone about 10%, and water 40% v/v;

b) methanol about 50%, 2-butanone (MEK) about 10%, and water 40% v/v;

c) methanol about 50%, cyclohexanone about 10%, and water 40% v/v;

d) ethanol about 50%, acetone about 10%, and water 40% v/v;

e) ethanol about 50%, 2-butanone (MEK) about 10%, and water 40% v/v;

f) ethanol about 50%, cyclohexanone about 10%, and water 40% v/v;

g) isopropanol about 50%, acetone about 10%, and water 40% v/v;

h) isopropanol about 50%, 2-butanone (MEK) about 10%, and water 40% v/v;

i) isopropanol about 50%, cyclohexanone about 10%, and water 40% v/v;

j) N-propanol about 50%, acetone about 10%, and water 40% v/v;

k) N-propanol about 50%, 2-butanone (MEK) about 10%, and water 40% v/v;

l) N-propanol about 50%, cyclohexanone about 10%, and water 40% v/v;

m) 2-butanol (SBA) about 50%, acetone about 10%, and water 40% v/v;

n) 2-butanol (SBA) about 50%, 2-butanone (MEK) about 10%, and water 40% v/v;

o) 2-butanol (SBA) about 50%, cyclohexanone about 10%, and water 40% v/v;

p) methanol about 30%, acetone about 30%, and water 40% v/v;

q) methanol about 30%, 2-butanone (MEK) about 30%, and water 40% v/v;

r) methanol about 30%, cyclohexanone about 30%, and water 40% v/v;

s) ethanol about 30%, acetone about 30%, and water 40% v/v;

t) ethanol about 30%, 2-butanone (MEK) about 30%, and water 40% v/v;

u) ethanol about 30%, cyclohexanone about 30%, and water 40% v/v;

v) isopropanol about 30%, acetone about 30%, and water 40% v/v;

w) isopropanol about 30%, 2-butanone (MEK) about 30%, and water 40% v/v;

x) isopropanol about 30%, cyclohexanone about 30%, and water 40% v/v;

y) N-propanol about 30%, acetone about 30%, and water 40% v/v;

z) N-propanol about 30%, 2-butanone (MEK) about 30%, and water 40% v/v;

aa) N-propanol about 30%, cyclohexanone about 30%, and water 40% v/v;

bb) 2-butanol (SBA) about 30%, acetone about 30%, and water 40% v/v;

cc) 2-butanol (SBA) about 30%, 2-butanone (MEK) about 30%, and water 40% v/v; and dd) 2-butanol (SBA) about 30%, cyclohexanone about 30%, and water 40% v/v.

4. The method of reducing a number of viable microorganisms in the flow path of claim 1, further comprising the steps of:

a) flowing a first fluid within said flow path prior to flowing a second fluid within said flow path, said second fluid being said antimicrobial composition;

b) displacing said first fluid by flowing a sufficient amount of said antimicrobial composition through said flow path; and c) flushing the flow path with said antimicrobial composition for a period of time between about 30 seconds and ten minutes.

5. The method of reducing a number of viable microorganisms in the flow path of claim 4, wherein said period of time of contacting said viable microorganisms with said antimicrobial composition is less than five minutes.

6. The method of reducing a number of viable microorganisms in a flow path of a microfluidic device of claim 1, wherein said microfluidic device comprises a flow cytometer.

7. The method of reducing a number of viable microorganisms in a flow path of a microfluidic device of claim 1, wherein said step of flowing an amount of an antimicrobial composition within said flow path comprises the step of flowing an amount of an antimicrobial composition, comprising:

i. 2-butanol between about 5% and about 70% by volume;

ii. 2-butanone between about 1.7% and about 35% by volume; and iii. water, wherein said alcohol and said ketone remain miscible in said water.

8. The method of reducing a number of viable microorganisms in a flow path of a microfluidic device of claim 7, wherein said antimicrobial composition is selected from the group consisting of:

a) 2-butanol about 5%, 2-butanone about 5%, and water 90% v/v;

b) 2-butanol about 7.5%, 2-butanone about 7.5%, and water 85% v/v;

c) 2-butanol about 8.3%, 2-butanone about 1.7%, and water 90% v/v;

d) 2-butanol about 10%, 2-butanone about 10%, and water 80% v/v;

e) 2-butanol about 12.5%, 2-butanone about 2.5%, and water 85% v/v f) 2-butanol about 16.5%, 2-butanone about 3.5%, and water 80% v/v;

g) 2-butanol about 30%, 2-butanone about 30%, and water 40% v/v; and h) 2-butanol about 50%, 2-butanone about 10%, and water 40% v/v.

* * * * *